US007097983B2

(12) United States Patent
Markovsky et al.

(10) Patent No.: US 7,097,983 B2
(45) Date of Patent: *Aug. 29, 2006

(54) METHOD FOR DETECTING THE PRESENCE OF AN ANALYTE IN A SAMPLE

(75) Inventors: Robert J. Markovsky, Amesbury, MA (US); Cheryl A. Boyer, Malden, MA (US); Stanley E. Charm, Boston, MA (US); Paul R. Donahue, Southboro, MA (US); Yael Agi Glickman, Moshav Tsofit (IL); Steven J. Saul, Arlington, MA (US); Joan L. Scheemaker, Chelmsford, MA (US); Richard T. Skiffington, North Reading, MA (US); Shefali B. Trivedi, Quincy, MA (US); Eliezer Zomer, Newton, MA (US)

(73) Assignee: Charm Sciences, Inc., Lawrence, MA (US)

( * ) Notice: Subject to any disclaimer, the term of this patent is extended or adjusted under 35 U.S.C. 154(b) by 200 days.

This patent is subject to a terminal disclaimer.

(21) Appl. No.: 09/961,998

(22) Filed: Sep. 24, 2001

(65) Prior Publication Data

US 2003/0207442 A1 Nov. 6, 2003

Related U.S. Application Data

(60) Division of application No. 09/118,135, filed on Jul. 16, 1998, now Pat. No. 6,319,466, and a continuation-in-part of application No. 09/001,775, filed on Dec. 31, 1997, now Pat. No. 5,985,675.

(60) Provisional application No. 60/088,937, filed on Jun. 11, 1998, provisional application No. 60/052,644, filed on Jul. 16, 1997.

(51) Int. Cl.
*G01N 33/53* (2006.01)
*G01N 31/00* (2006.01)
*G01N 33/558* (2006.01)

(52) U.S. Cl. .................. 435/7.1; 435/7.92; 435/970; 435/805; 436/8; 436/15; 436/501; 436/514; 436/535; 436/524; 436/536; 422/56; 422/60; 422/61

(58) Field of Classification Search .................. 435/7.1, 435/7.92, 970, 805; 436/501, 514, 530, 535, 436/536, 524, 525, 8, 15; 422/56, 60, 61
See application file for complete search history.

(56) References Cited

U.S. PATENT DOCUMENTS

| 4,700,714 | A |   | 10/1987 | Fuisz |
| 4,703,017 | A |   | 10/1987 | Campbell et al. ........... 436/501 |
| 4,743,560 | A |   | 5/1988  | Campbell et al. ........... 436/501 |
| 4,826,759 | A |   | 5/1989  | Guire et al. .................. 435/4 |
| 4,999,285 | A |   | 3/1991  | Stiso ........................... 435/7.9 |
| 5,158,869 | A | * | 10/1992 | Pouletty et al. .............. 422/58 |
| 5,238,652 | A |   | 8/1993  | Sun et al. ..................... 422/61 |
| 5,260,222 | A |   | 11/1993 | Patel et al. ................... 436/180 |
| 5,266,497 | A |   | 11/1993 | Imai et al. .................... 436/514 |
| 5,296,347 | A | * | 3/1994  | LaMotte, III ................ 435/5 |
| 5,434,053 | A |   | 7/1995  | Piasio |
| 5,451,504 | A |   | 9/1995  | Fitzpatrick et al. .......... 435/7.2 |
| 5,521,102 | A |   | 5/1996  | Boehringer et al. |
| 5,545,721 | A | * | 8/1996  | Carroll et al. ............. 530/391.7 |
| 5,591,645 | A |   | 1/1997  | Rosenstein ................... 436/514 |
| 5,602,040 | A |   | 2/1997  | May et al. .................... 436/514 |
| 5,622,871 | A |   | 4/1997  | May et al. .................... 436/514 |
| 5,656,448 | A |   | 8/1997  | Kang et al. |
| 5,714,389 | A |   | 2/1998  | Charlton et al. ............. 436/514 |
| 5,726,010 | A |   | 3/1998  | Clark ............................. 435/5 |
| 5,726,013 | A |   | 3/1998  | Clark ............................. 435/5 |
| 5,739,041 | A |   | 4/1998  | Nazareth et al. |
| 5,753,517 | A |   | 5/1998  | Brooks et al. ................ 436/514 |
| 5,766,962 | A | * | 6/1998  | Childs et al. ................. 436/518 |
| 5,874,216 | A | * | 2/1999  | Mapes ........................... 435/6 |
| 5,962,339 | A | * | 10/1999 | Midgely ........................ 436/534 |
| 6,001,658 | A |   | 12/1999 | Fredrickson |
| D419,439  | S |   | 1/2000  | Markovsky et al. |
| 6,177,281 | B1| * | 1/2001  | Manita et al. ................ 436/518 |
| 6,319,466 | B1| * | 11/2001 | Markovsky .................. 422/56 |

FOREIGN PATENT DOCUMENTS

| EP | 0 279 574 A1 | 8/1988 |
| EP | 0 291 176 B1 | 11/1988 |
| EP | 0 291 194 B1 | 11/1988 |
| EP | 0 299 428 A2 | 1/1989 |
| EP | 0 306 336 A2 | 3/1989 |
| EP | 0 321 145 A2 | 6/1989 |

(Continued)

OTHER PUBLICATIONS

Brady et al., Journal of Food Protection, 56(3):229-233, Mar. 1993.
Charm et al., Journal of the Association of Food and Drug Officials, 58(1), 17-29, Jan. 1994.
Charm et al., J. Assoc. Off. Anal. Chem., 71(2), 1988.

(Continued)

*Primary Examiner*—Long V. Le
*Assistant Examiner*—Jacob Cheu
(74) *Attorney, Agent, or Firm*—Leslie Meyer-Leon; IP Legal Strategies Group P.C.

(57) ABSTRACT

The invention features a method of determining whether one or more members of an analyte family are present in a sample. The method makes use of a test zone binder, e.g., a receptor that can bind one or a plurality of analytes within an analyte family, the analytes family defined by similar structural binding sites. Members of an analyte family can have different detection level requirements and, therefore, additional analyte binders can be employed to adjust test sensitivity for a subset of the analytes in the analyte family individually, so that each analyte can be detected only if it is present in the sample above a predetermined threshold.

47 Claims, 10 Drawing Sheets

FOREIGN PATENT DOCUMENTS

| | | |
|---|---|---|
| EP | 0 378 391 | 7/1990 |
| EP | 0 516 095 A2 | 12/1992 |
| EP | 0 582 231 A1 | 2/1994 |
| EP | 0 593 112 B1 | 4/1994 |
| EP | 0 284 232 B1 | 6/1995 |
| GB | EP 0593112 * | 9/1993 |
| WO | WO 90/15327 | 12/1990 |
| WO | WO 93/17338 A1 | 9/1993 |
| WO | WO 94/02850 | 2/1994 |
| WO | WO 96/38720 | 12/1996 |
| WO | WO 97/03209 | 1/1997 |
| WO | WO 97/05287 | 2/1997 |

OTHER PUBLICATIONS

Hassnoot et al., "Evaluation of a Sol Particle Immunoassay (SPIA) Based Single-Step Strip Test for the Dectection of Sulfadimidine Residues," Euro Residue III (1996) 461-465.

"A Short Guide—Developing Immunochromatographic Test Strips," 1996, Lit. No. TB500, Millipore Corporation, Bedford, MA, USA.

Verheijen et al., "Single-Step Strip Tests for Residue Analyses," DLO-State Institute for Quality Control of Agricultural Products (RIKILT-DLO) (Jun. 3, 1998).

European Search Report, dated Aug. 20, 2004, for EP Application No. 04 00 4322.6.

* cited by examiner

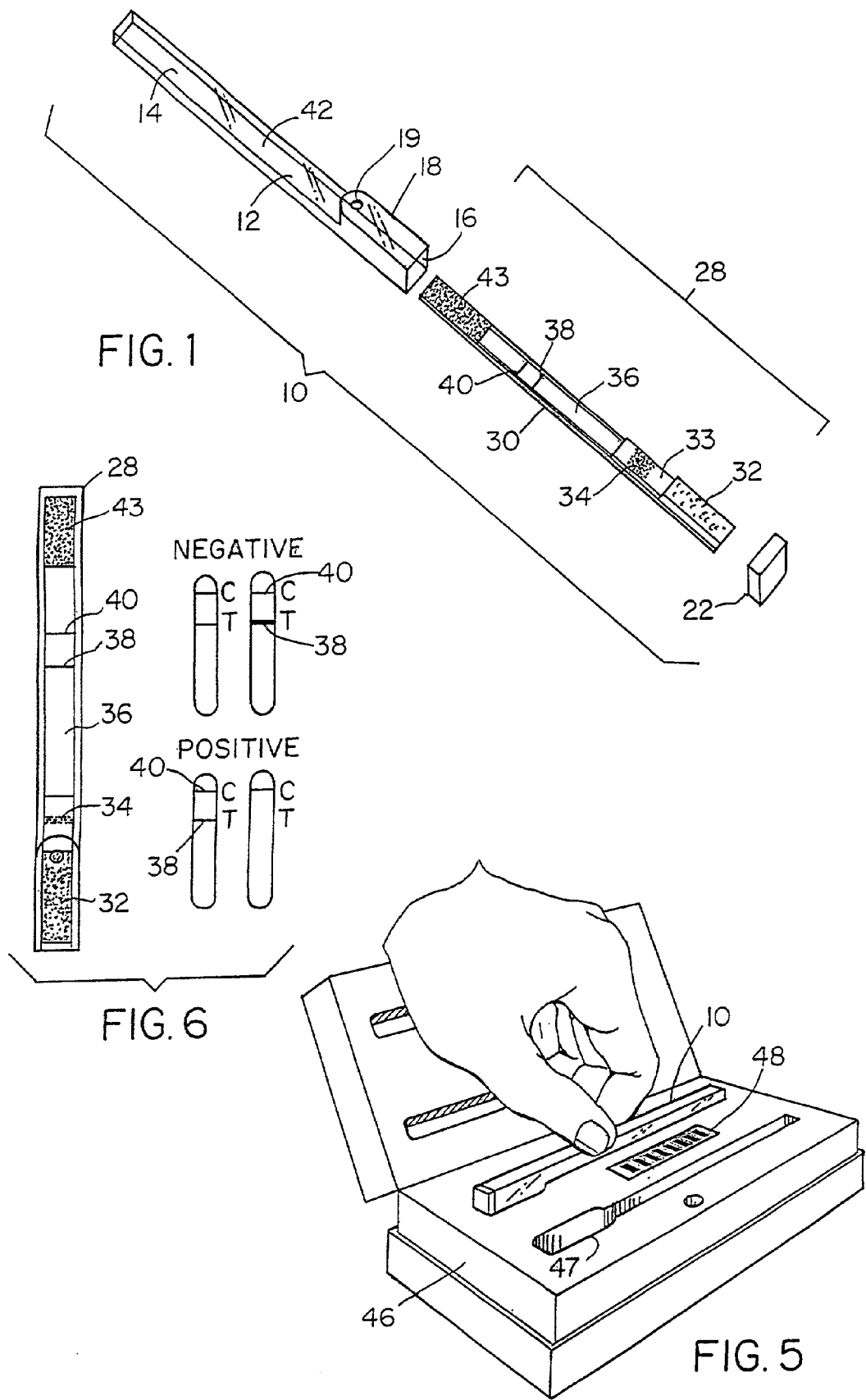

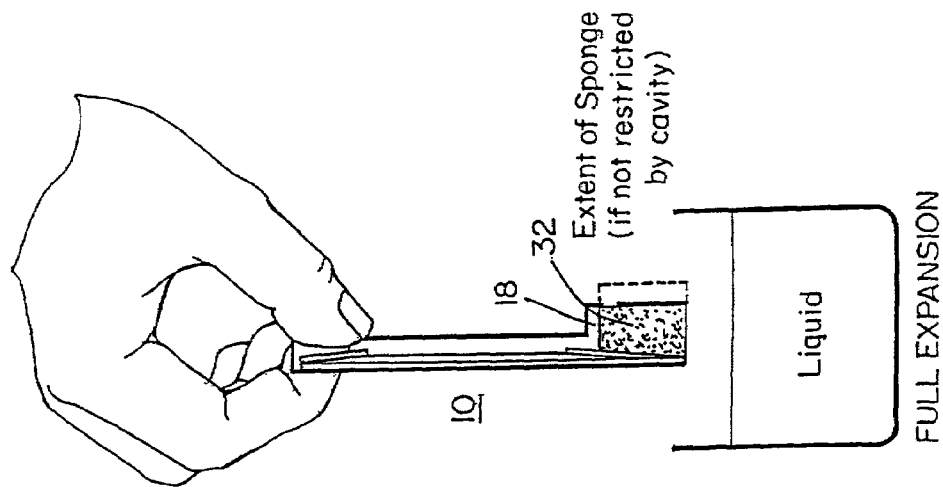
FIG. 4 FULL EXPANSION
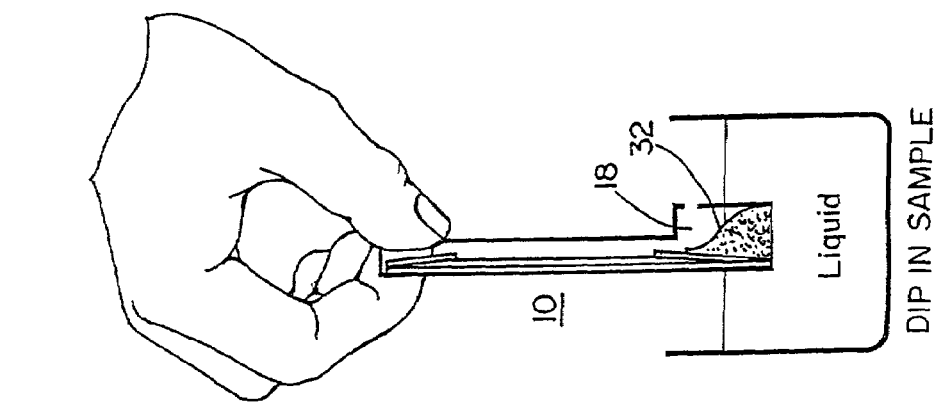
FIG. 3 DIP IN SAMPLE
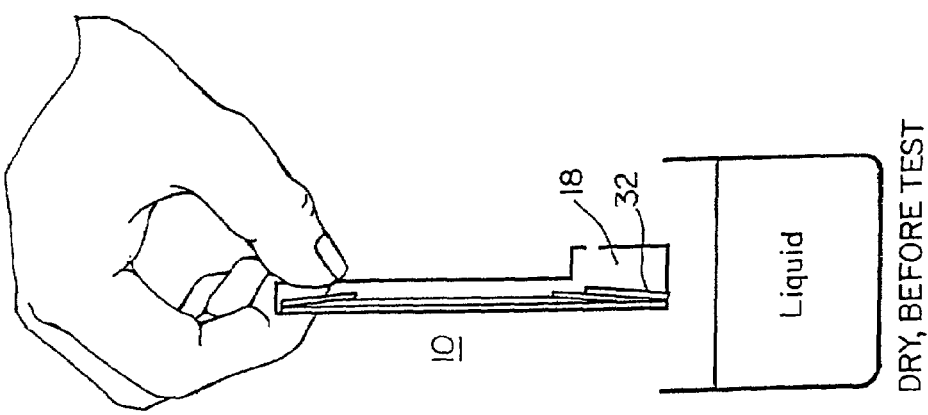
FIG. 2 DRY, BEFORE TEST

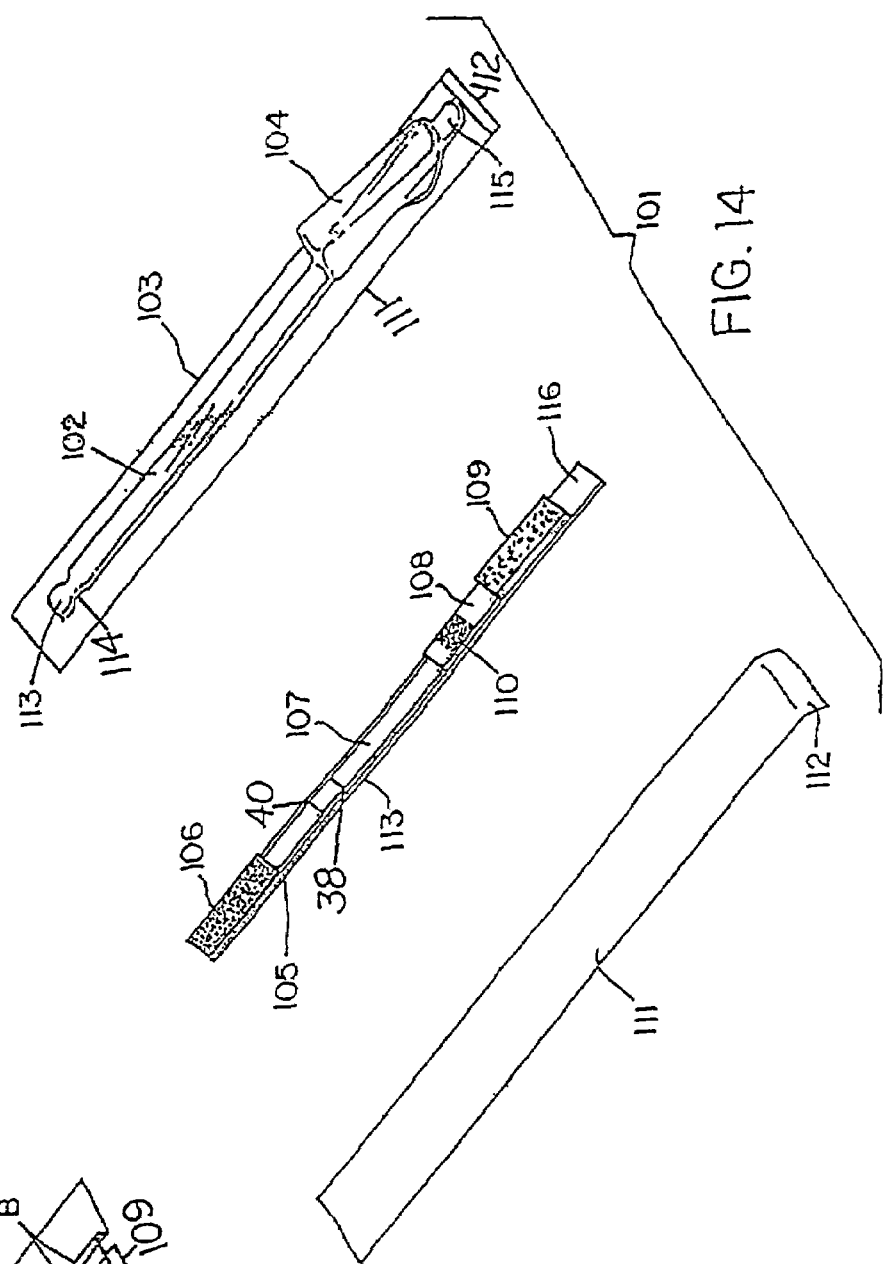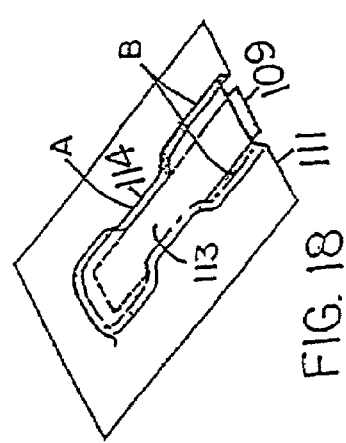

Figure 20
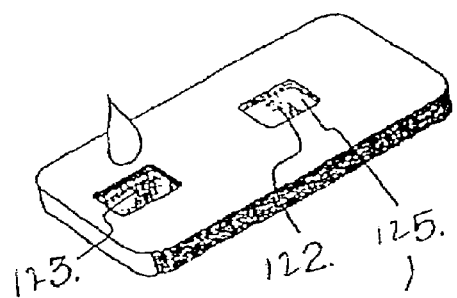
Figure 21
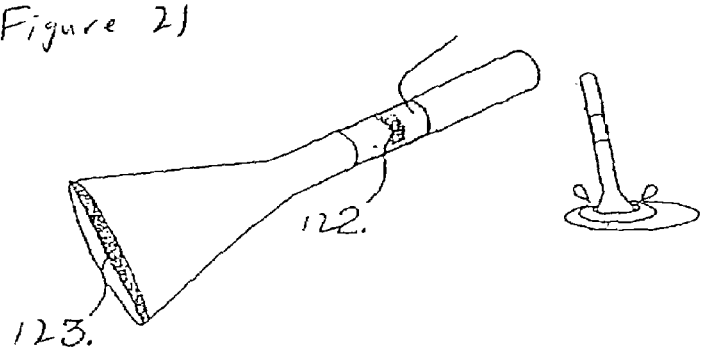
Figure 22
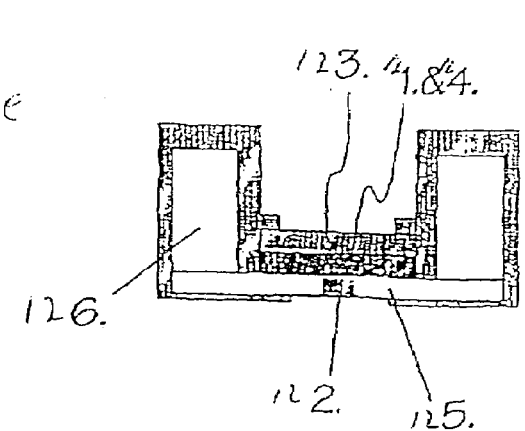 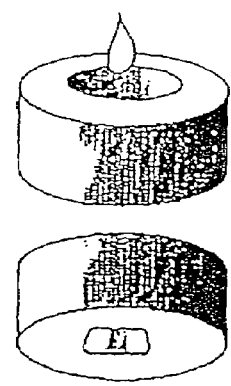

METHOD FOR DETECTING THE PRESENCE OF AN ANALYTE IN A SAMPLE

REFERENCE TO PRIOR APPLICATIONS

This application is a divisional application of U.S. patent application Ser. No. 09/118,135, filed July 16, 1998, now U.S. Pat. No. 6,319,466, issued Nov. 20, 2001, which application claimed the benefit of U.S. Provisional Patent Application Ser. Nos. 60/052,644 filed on Jul. 16, 1997, and 60/088,937, filed on Jun. 11, 1998, and which application was a continuation-in-part of U.S. patent application Ser. No. 09/001,775, filed Dec. 31, 1997, now U.S. Pat. No. 5,985,675, issued Nov. 16, 1999, which applications are all incorporated herein by reference in their entirety.

BACKGROUND OF THE INVENTION

Lateral-flow or immunochromatographic test kits and methods for the detection of the presence or concentration of chemical residues or analytes or classes thereof from liquid samples have been developed. An example of one such test kit includes a pregnancy test kit, for example, U.S. Pat. No. 5,266,497. Similar devices are used for chemical residue detection utilizing an enzyme conjugate, for example, U.S. Pat. No. 4,999,285. For antibiotics, IDEXX has been using a two element-assay including a test tube (containing enzyme-conjugate receptor) and a lateral-flow device (containing immobilized analyte). This device has been commercially marketed as the SNAP test. In addition, competition assays for drugs in urine and serum have been described using 0.1–1 µm color beads with sensitivity levels of 300 ppb (Sun et al. U.S. Pat. No. 5,238,652). All these assays have the drawback that they are overly sensitive for some residues which has the potential to result in a sample testing positive that is actually acceptable by the regulations as negative. The current invention will correct this problem, while simplifying the test and making it more acceptable as a screening test to regulatory, industry, and consumer entities.

Particularly in the food safety area, it has long been recognized that residue detection should be accurate, inexpensive and easily conducted. Consumers and governments are becoming increasingly aware of the necessity for testing foods for the presence of undesirable residues naturally occurring or otherwise.

Since a large portion of the consumers are children, food safety has long been critical in the dairy industry. Antibiotic residues used on a dairy farm occasionally appear in the milk supply. The hazards associated with these undesirable residues include: allergic reactions, assisting the propagation of new and sometimes drug-resistant microorganisms and other long term health risks.

Government agencies have established, in some cases, legal limits for particular-residues in foods, for example, antibiotic residues in milk. Residues above the "legal" limit are considered unsafe for human consumption. Residue levels below the legal limit are considered "safe". It is important, therefore, that detection methods, in addition to being inexpensive and easily conducted, do not give positive results when residues are below legal limits, so that otherwise acceptable milk, or other foods, are not discarded or otherwise treated as containing residues above legal limits.

SUMMARY OF THE INVENTION

The invention relates to an analyte or chemical residue test device and method employing a lateral-flow test strip for the detection of the analyte or residue in a sample and a method therefor.

Often liquids, such as milk, meat extract, serum, or environmental samples in the field or in the lab have one or more contaminants or analytes that are in trace amounts that need to be assayed. In order to detect the analyte, the present invention employs a labeled receptor that reacts with the analyte to form an analyte-receptor complex. Examples of such receptors include biological receptors similar to the ones described in U.S. Pat. No. 4,239,852 and specifically designed broad spectrum antibodies to detect veterinary drugs or tagged receptor, which was previously stabilized with readily soluble additives, is positioned within or proximate to a membrane and when exposed to the liquid, lateral capillary flow occurs thereon. In one example, the time controlled released tagged-receptor reacts with the analyte in the sample while moving into the reaction or test zone. In the flow, the liquid carries the analyte-receptor complex, and any unbound labeled receptor with it. Positioned on the membrane in the flow path is a test zone. The test zone has a representative analyte conjugate attached to the membrane, to bind an unbound receptor to form a first analyte conjugate receptor complex that, as a result of the label, has a signal visible to the eye or readable with an instrument.

Capillary flow of the liquid continues on the membrane to a control zone. The control zone includes a binder attached to the membrane that binds with the labeled receptor. Upon binding, the control zone changes to a signal that can be visible to the eye or readable with an instrument or visible under special light conditions, such as ultraviolet. If the signal in the test zone is more intense than the signal in the control zone, the test indicates that the analyte is not present in a sufficient amount (a negative test). If the test zone signal is less intense than the control zone signal, the test indicates that the analyte is present in an amount in excess of allowable levels (a positive test).

The receptor may bind a family of analytes (one or a plurality of analytes) which have similar structural binding sites. Members of an analyte family can have different detection level requirements and, therefore, additional analyte binders can be employed, for example, monoclonal or polyclonal antibodies, that bind a portion of the analyte in competition with the receptor, in the sample, thereby decreasing test sensitivity. The antibodies are mixed with the labeled receptor in an amount to adjust the sensitivity for a specific analyte or group of analytes. The sensitivity of the test is adjusted so that a positive test result is not given unless a certain threshold of analyte is present in the sample. In one example, initial sensitivity of a beta-lactam receptor to cephapirin is 5 ppb (parts per billion), by including specific antibodies to cephapirin, the sensitivity was adjusted to 15–20 ppb (regulatory level is 20 ppb).

The test device includes a support strip and a sample-absorbing matrix attached to the support strip. The sample-absorbing matrix is a material for absorbing an amount of the sample, for example, a sponge. Sponges can be made from, for example, cellulose or synthetics such as MEROCEL® sponges (MEROCEL is a registered trademark of Merocel Corporation of Mystic, Connecticut), polyvinyl acetal polymer (PVA), porous polyethylene, or other mixture of fibers. Such sponges are sized to absorb a fixed amount of sample as required to complete the assay. The sample-absorbing matrix, or pads, in some embodiments, can be used to control the sample flow and filter particulates that might interfere with the flow. In some embodiments, the sample-absorbing matrix can include or be adjacent to a buffering zone. The test device also includes a mobile-phase support for holding a mobile-phase composition. The mobile-phase support is attached to the support strip and is in contact with the sample-absorbing matrix. A mobile-phase composition is disposed within or on the mobile-phase support and has a labeled receptor for binding with the analyte. The mobile-phase composition can be carried in the sample and flow together with the sample. A stationary-phase membrane is attached to the support strip and has a first membrane end in contact with the mobile-phase composition and a second membrane end in contact with the disposal zone. The membrane allows lateral capillary flow of the sample from the first membrane end to the second membrane end. A test zone is on the stationary-phase membrane between the first membrane end and second membrane end and has an analyte conjugate for binding with an unbound labeled receptor. A control zone is on the stationary-phase membrane between the test zone and second membrane end and has a binder, for example, an antibody to the particular receptor, for binding with an analyte-bound receptor and excess unbound receptor.

The invention also includes an analyte test device for detecting, in a general horizontal position, an analyte in a liquid sample by capillary lateral flow in a chromatographic test strip. The device incudes an elongated housing defining an elongated strip cavity having an open application aperture at one end and having another end. The cavity is adapted to receive and hold a test strip therein. The housing has a transparent top cover section to allow the observation of test results on the test strip. The housing is characterized by an enlarged application cavity extending outwardly from the top cover and having or adapted to have an open end at the application end. The test device includes a test strip positioned in the strip cavity.

The test strip includes a support strip with a plurality of sequential contacting, liquid-sample, permeable zones extending from the first end to the second end. The zones allow the lateral capillary flow of the liquid sample from the first end to the second end. The zones include a sample-absorbing and filtering zone composed of an expandable, porous, compressed-material layer which moves, on contact with the liquid sample, between a nonexpanded state to an expanded state on absorption of a preselected amount of the liquid sample, and a mobile-phase support having a mobile-phase composition layer thereon or therein with a labeled receptor for binding the analyte in the liquid sample thereon, typically a visible area containing colored beads and a membrane generally of nitrocellulose which includes a reaction zone having at least one stationary analyte conjugate reference or test line, or generally a test and a separate control line thereon, and optionally a disposal zone of liquid-sample absorbent material to absorb less liquid sample and to aid in capillary flow to the second end.

The sample-absorbing zone with the compressed material layer is positioned adjacent the application cavity. The compressed-material layer and the application cavity are designed to allow the compressed-material layer to absorb a selected amount of liquid sample for testing and in an amount sufficient to carry out the test and to expand from a dry, nonexpanded form to a wet, expanded state. The material layer in a wet, expanded state fills substantially the application cavity and causes sufficient pressure on the housing walls of the expansion cavity to drive capillary flow of the liquid sample in the application cavity to a selected volume when the open application end of the test device is inserted into a liquid to obtain the liquid sample or when a known amount of sample is pipetted into the application cavity.

In one embodiment, a housing is employed, such as a one-piece, integral, injection-molded, all-transparent, plastic material, with the plastic material selected or designed to be subject to incubator temperatures of 30° C. or more for incubation times, for example, 2 to 10–15 minutes, depending on the particular test, although not all tests will require incubation at temperatures other than room temperature.

In one embodiment, the housing includes a generally toothbrush shape, with an enlarged (generally triangular when side-viewed), toothbrush-type head at the open application end of the housing, with a dry, inert, porous, expanded, liquid-permeable, absorbing material as an absorbing zone in the test strip, for example, of cellulose or nitrocellulose, positioned beneath the open bottom of the application cavity or chamber. The absorbing layer, on contact, such as immersion of the application end of the housing of the test device in a liquid, absorbs a preselected amount of the liquid sample necessary for the test. The absorbing-layer material expands, for example, in one to thirty seconds, to fill or substantially fill the expansion cavity and contact the surrounding walls of the expansion-cavity housing, to cause sufficient pressure within the expansion cavity and the expanded state of the material, to drive capillary flow laterally in the underlying test strip laterally toward the end of the elongated housing where the test strip is positioned. The expansion cavity and underlying absorbing-layer material, which generally mimics two dimensions of the expansion cavity, permit absorbing and filtering of the selected amount of liquid sample for the test strip. The expansion cavity and absorbing-layer material aid in driving the lateral flow of the liquid sample in the test strip in the housing toward the disposal zone at the end of the strip to receive the liquid sample where employed. If the absorbing layer does not expand sufficiently to fill or substantially fill the expansion cavity, the lateral or capillary flow rates and times can be unsatisfactory. The flow rate can be too slow and the time period can be too long. If the absorbing layer is used in excess, then excess pressure occurs in the expansion cavity, and the expanded absorbing layer tends to retard the desired lateral flow of the liquid sample.

The housing with the toothbrush-shaped design can include a separate injection-molded housing with an optional end cover, to protect the exposed application end before sampling and after sampling, and in the incubation chamber, to prevent cross-contamination from other sources. The test device with the molded housing allows the user to handle the handle end of the housing and to obtain a liquid sample merely by dipping the open application cavity into a liquid.

The housing can include a toothbrush-shaped design, wherein the expansion cavity is formed in a plastic, usually transparent, blister-type package which is sealed against a flat support, such as a paper strip or another plastic strip, and which encompasses within the blister package the selected test strip. The blister package includes a removable seal strip at the one application end of the enclosed test strip for peeling or removal prior to use and for the introduction of a selected volume of the liquid to the application-absorbing zone of the test strip while in the blister package, e.g., by pipetting. The blister package with the liquid sample and test strip can be incubated in the incubator and the test results observed visually or read by an instrument.

In another embodiment, it has been discovered to be desirable to provide one or more apertures in the housing which defines the expansion cavity, to permit the time-controlled and more rapid absorbing of the liquid sample into the absorbing material for more efficient absorption and to reduce absorption time of the liquid sample. In particular, one or more apertures should be placed on the top cover or surface of the expansion-cavity housing, particularly of the molded housing, rather than on the sides, so that entrapped air after immersion is discharged from the expansion cavity, as the absorbing layer expands into the wet, absorbing, expanded state. While a flat, rectangular strip of absorbing material is shown with a generally rectangular expansion cavity which mimics and provides for the expanded, rectangular strip of the absorbing zone, it is recognized that the size, material, dimensions and shape of the absorbing material and the shape or form of the expansion cavity may vary in the practice of the invention. Typically, the open bottom of the expansion cavity is directly above the absorbing layer and usually of about the same width and length dimensions, to permit expansion without restriction of the absorption layer into the expansion cavity.

While a fully transparent top cover is desirable to enclose the test strip and observe or read the test results on the test strip, it is recognized that the top cover can be open or have an aperature to view the test results, or only a section of the top cover be transparent to view the test results, or where applicable the housing may be modified, so that the test results can be determined by optical or electronic instrument means.

The test device can be packaged for use in a blister-type package or employ a fixed or slidable protective cap at the application end, to protect the test device from contamination prior to use and to protect the test device after contact with the liquid sample and in the incubator (where required in the test), to protect against cross-contamination. The protective cap can be removable and enclose totally the application end of the housing, or merely be slidably extended outwardly from the application end between a retracted use position and extended, protective, closed position.

The test device employs a test strip selected to detect the presence or concentration of selected analytes or residues, either a single residue or classes thereof, and visually by reference of a reaction test zone or reference line in the test strip which may be observed or measured. Usually, a control zone or line is spaced apart slightly downstream from the reference zone or lines for control purposes. The housing of the test device is applicable to a wide variety of present employed or described test strips which are based on lateral flow or capillary flow, regardless of the nature of the particular analyte-residue test, provided only that the application or liquid contact portion of the test strip requires or uses a filtering absorbing material which moves by liquid-sample contact between a nonexpanded and an expanded state at or toward the one application end of the test device. Typically, the test strip has a support and includes on one surface a plurality of contacting, liquid-permeable, sequential zones or sections with a stationary zone, a mobile zone and, optionally, a disposal zone. The test device is particularly useful in connection with the liquid sample comprising a fluid, for example, urine, blood, milk or corn extract and in the detection of antibiotics, like beta-lactams, toxins, viruses, bacteria, pesticides and the like. However, the test device can employ one or more test strips directed to a variety of tests.

In another embodiment, the analyte test device includes an elongated housing defining an elongated strip cavity having two ends. The cavity is adapted to receive and hold a test strip and has a transparent, top-cover section to permit the observation of test results on the test strip. The elongated housing: is slightly wider than the width of the test strip in the area where sample flow occurs; includes a narrowing of the housing in areas where lateral flow does not occur; and has an enlarged application cavity extending outwardly from the top cover. The test strip is positioned in the strip cavity and includes a support strip with a plurality of sequential, contacting, liquid-sample, permeable zones. Lateral capillary flow of the liquid is through each zone from one end of the test strip to the other end. The zones include: (i) a sample-absorbing zone composed of an expandable, porous, compressed-material layer which moves on contact with the liquid sample between a dry, non-expandable state to a wet, expandable state, on absorption of the liquid sample; ii) a releasing zone having a mobile-phase layer thereon with a receptor, for example a protein or monoclonal antibody for the analyte attached to a mobile visible marker; iii) a reaction zone having one or more stationary-layer, analyte reference lines thereon for observation, and, optionally, a control line spaced apart from the reference line, to detect the presence or absence of analyte in the liquid sample; and iv) an optional disposal zone of a layer of liquid-sample absorbent material for the liquid sample, to induce capillary flow to the second end. The sample-absorbing zone with the compressed-material layer is positioned adjacent the application cavity. The application cavity is dimensioned and designed so that the compressed-material layer absorbs a selected amount of liquid sample to be tested that is sufficient to carry out the test. Upon sample application, the compressed-material expands from a dry, non-expandable state to a wet expanded state. When the material layer is in the wet, expanded state it substantially fills the cavity thereby driving capillary flow of the liquid sample toward the disposal zone in said strip in a selected time period. The test device further includes means to removably seal the application end of the housing.

Where applicable, the test device is employed in combination with an incubator, such as a portable, electrically heated incubator with an incubation chamber which can be dimensioned to receive the test-device housing snugly therein for heating for a selected incubator time, for example, at a temperature in the range of between about 45 and 75° C., preferably between 55 to 65° C., and for a period of 1 to 10–15 minutes. The test device and incubator also include a timer, so that the incubation period can be timed by a user.

In operation, the test device with a protective covering or cap has the cover or cap removed and the application end contacted with a liquid to be tested, such as by immersion, for about one to ten seconds and then removed, or a liquid sample pipetted into the application end. The absorbing material is allowed to expand within the expansion cavity, for example, one to fifteen seconds, then the test device is placed in an incubator for a time period, then removed and the test results observed or measured. If the sample is pipetted the device is placed in the incubator and the sample is pipetted into the sample cavity.

The present invention includes many advantages, such as combining high purity broad spectrum receptors or antibodies with high specific activity per surface area combined with counteracting residue specific antibodies (e.g., monoclonal) to achieve residue detection on the order of parts per billion (ppb) ($10^{-9}$) or parts per trillion (ppt) ($10^{-12}$) levels at or close to regulatory requirements. Targeting the active moiety of the chemical residue allows detection of a broad spectrum of active pharmaceuticals (e.g., veterinarian drugs), agricultural chemicals (e.g. pesticides), or microbial toxins and their active metabolites. Further, additional antibodies can be added to adjust the threshold sensitivity of the test.

Other advantages include that all components can be incorporated in the device and reagent preparation is not necessary. The device is a one-step assay that does not require timing (results are stable from about four minutes to a few hours). The device, which has a built-in negative control, eliminates the need for external control standards.

BRIEF DESCRIPTION OF THE DRAWINGS

FIG. 1 is a perspective, exploded view of a molded-housing test device.

FIGS. 2, 3 and 4 are schematic, illustrative views of the use of the test device of FIG. 1.

FIG. 5 is a perspective view of an incubator and the test device with a liquid sample.

FIG. 6 is an enlarged, front-plan view of the test strip of FIGS. 1–5, with enlarged, front, sectional views of positive and negative test results.

FIG. 14 is a perspective, exploded view of a blister-pack test device with protruding backing and narrowing of the blister to produce pinch points.

FIG. 18 is an enlarged, perspective view of the strip movement restriction zone of FIG. 14.

FIGS. 20, 21, and 22 illustrate alternative test device packaging embodiments including: a standard lateral-flow device, such as is used in the pregnancy testing industry (FIG. 20); vertical probe (FIG. 21); and sandwich-type device (FIG. 22).

DETAILED DESCRIPTION OF THE INVENTION

Figure 8:
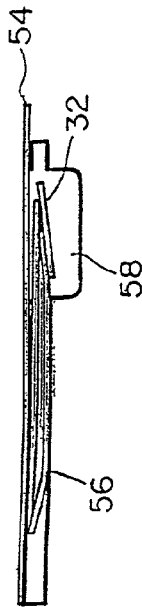
FIGS. 8, 9 and 10 are schematic, illustrative, side views of the use of the test device of FIG. 7.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention. All percentages and parts are by weight unless otherwise indicated.

The present invention relates to a test device and method for detecting the presence of a residue analyte in a sample. The test and device use direct color, fluorescence, luminescence, or infrared recognition-based broad spectrum assays to rapidly detect low part per billion (ppb) presences of a chemical or a family of chemical residues sharing common recognition sites. The kits are designed for testing antibiotics, toxins and pesticides in food or environmental samples in the field, or in the lab. The assays are noncompetitive using saturation chemistry.

In the drawings, FIGS. 1–6 show analyte test device 10 which includes elongated, molded housing 12. Housing 12 can be formed of a one-piece, injection-molded, transparent styrene polymer. Housing 12 defines elongated housing cavity 14 with open end 16, and having enlarged, rectangular application expansion cavity 18 at open end 16 of housing 12. Housing 12 includes an elongated bottom cavity formed during the injection-molding process. The housing includes an optional removable, friction-fitted or snap-on protective cap 22 adapted to fit over open end 16 of housing 12 and liquid expansion apertures 19 in the top cover of the application housing cavity to increase the efficiency of expansion of a sample-absorbing matrix, such as sponge 32, within the test time.

Housing cavity 14 includes therein on the bottom surface a lateral-flow test strip 28 adapted to detect the presence of an analyte in a liquid sample, such as milk. Test strip 28 includes support strip 30 with sponge 32 attached at one end. Sponge 32 can include a plurality of sequential layers comprising a rectangular pad of dry, compressed, cellulosic material as a liquid-sample absorbent secured to the face surface of the support strip 30. Sponge 32 is selected to expand in contact with the liquid, such as milk, to fill the expansion cavity 18, which sponge 32 mimics in two dimensions. For example, with milk, sponge 32 is about 3–4 mm by 12–14 mm, while cavity 18 is about 5–6 mm by 15–16 mm by 4–6 mm in height. Expansion cavity 18 can be dimensioned about 60% to 30% less than the full expansion of the sponge material.

Support strip 30 includes treated, mobile-phase support 33 with mobile-phase composition 34, stationary-phase membrane 36, which includes test zone 38 and control zone 40 for the analyte to be detected, and disposal zone 43 at the second end of support strip 30 to capture excess liquid sample. Housing 12 includes transparent top cover 42 for visual observation of test zone (reference zone) 38 and control zone 40. Test strip 28 is placed and positioned loosely in the elongated cavity 14, with sponge 32 positioned beneath the expansion cavity 18, and sponge 32 extending generally to about or slightly beyond the plane of the open application end, and the end covered prior to use by protective cap 22.

In operation, protective cap 22 is removed prior to use and the open application end of housing 12 inserted briefly (about one to ten seconds) in the liquid, such as milk, to be tested employing elongated housing 12 as a handle (see FIG. 2). Test device 10 is removed and sponge 32 is allowed to expand to fill expansion cavity 18 and to start the lateral flow of the milk sample through test strip 28 (2 to 6 minutes) (see FIGS. 3 and 4). Preferably, protective cap 22 is inserted to protect against cross-contamination, and test device 10 then placed in a horizontal position, with the application cavity 18 extending downwardly in an electric-heated incubator 46 with incubator cavity 47 shaped to receive the test device, and incubation carried out, for example, for three to ten minutes. The incubation temperature is observed through the temperature-indicator scale 48 (see FIG. 5). Incubated test device 10 is then removed and reversed, and the front view of the test device with test zone 38 and control zone 40 observed (see FIG. 6). The line readings for positive and negative controls are illustrated in FIG. 6 adjacent the front view of test device 10. In sponge 32, expansion is controlled by the expansion cavity 18 volume and size, resulting in sponge 32 completely filling expansion cavity 18 with a preselected volume of liquid, for example, 0.1 to 1.0 ml, so the amount of liquid sample taken in for the test is controlled to the correct amount. The dimensions of expansion cavity 18 prevent the sponge pad 32 to fully expand, so that pressure is maintained in the expanded sponge, as shown in FIG. 4, to aid in forcing capillary-lateral flow of the liquid sample through the test strip 28 in the housing 12.

The drawings in FIGS. 7–13 illustrate another embodiment of test device 50 in a transparent blister package, which includes transparent-tape plastic seal strip 52 with peel tab 54 at one end, and transparent blister package 56 adhesively secured to strip 52, to enclose test strip 28 therein. Blister package 56 includes an elongated cavity to hold strip 28 and an expansion cavity-housing 58 at the one end to form a generally toothbrush-shaped cavity within plastic blister package 56 and strip 52. Selected test strip 28 is sealed and enclosed within blister package 56.

Figure 9:
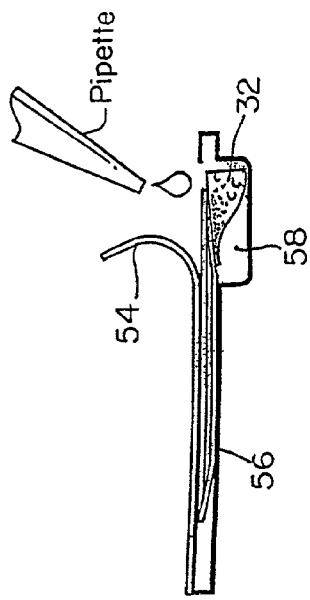
Figure 7:
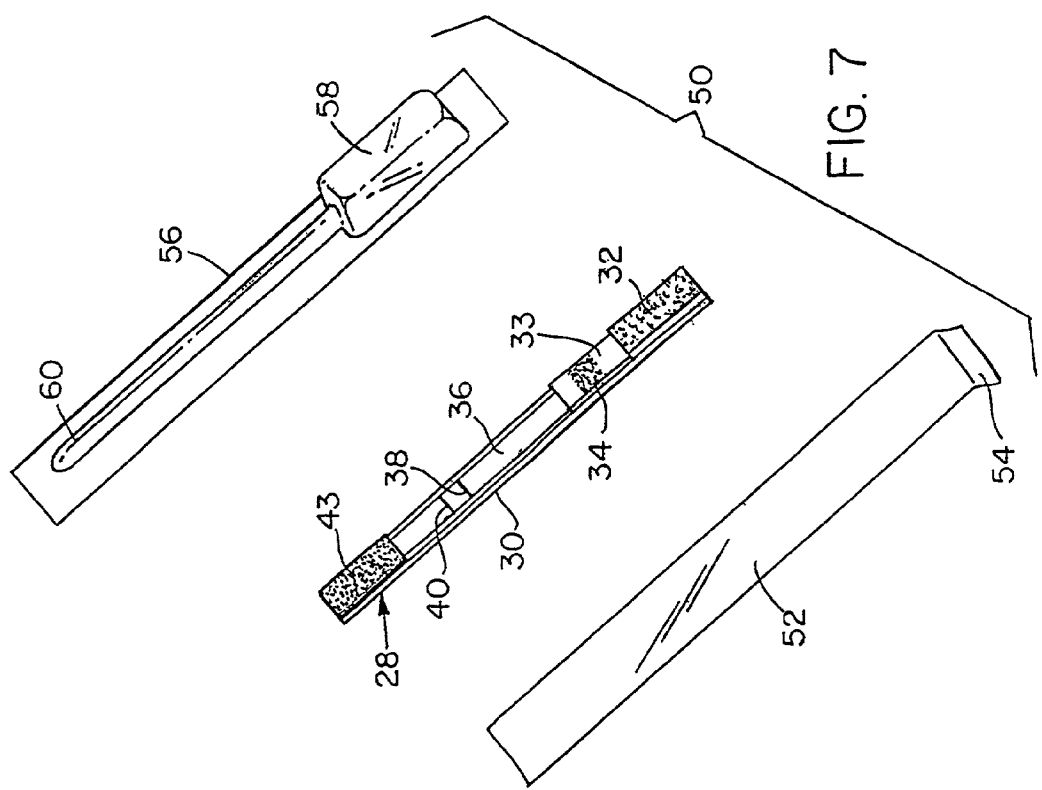
FIG. 7 is a perspective, exploded view of a blister-pack test device.

FIG. 8 shows a side sectional view of the blister-package test device 50 prior to use. FIG. 9 shows blister-package test device 50 with one end peeled back by peel tab 54, to expose expansion housing cavity 58 and sponge 32 of test strip 28, so that a defined amount of a liquid sample can be added, for example, by pipet, as shown. In a preferred embodiment, cavity 18 is shaped similar to sponge 32, as shown in FIG. 7.

Figure 10:
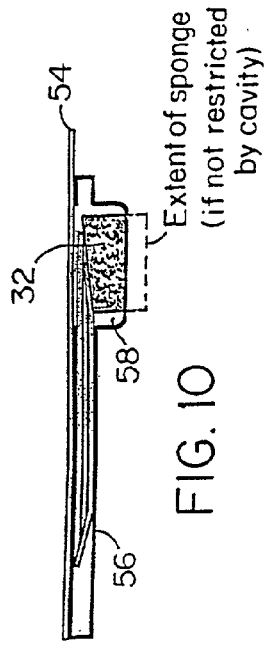

FIG. 10 illustrates test device 50 after addition of the liquid sample, and with peel tab 54 resealed, and with sponge 32 fully expanded by the liquid sample within housing cavity 58, and ready to incubate.

Figure 11:
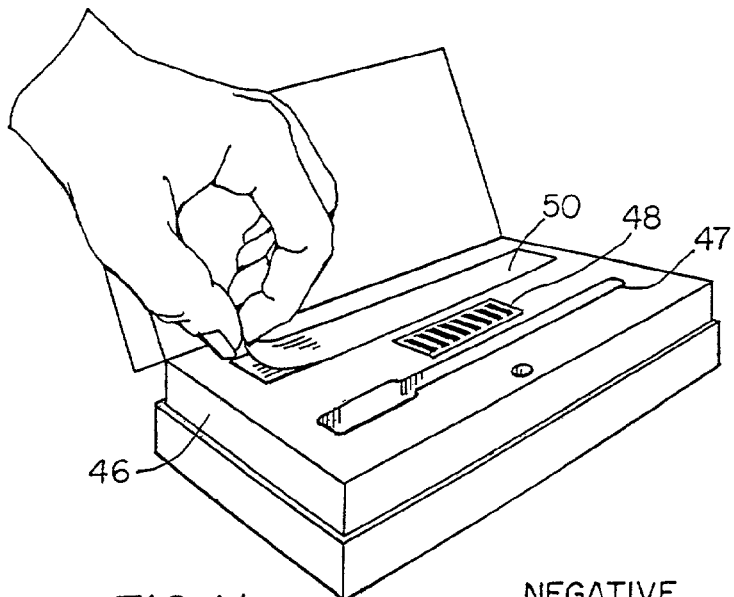
FIGS. 11 and 12 are perspective views of an incubator and the test device with a liquid sample.
Figure 13:
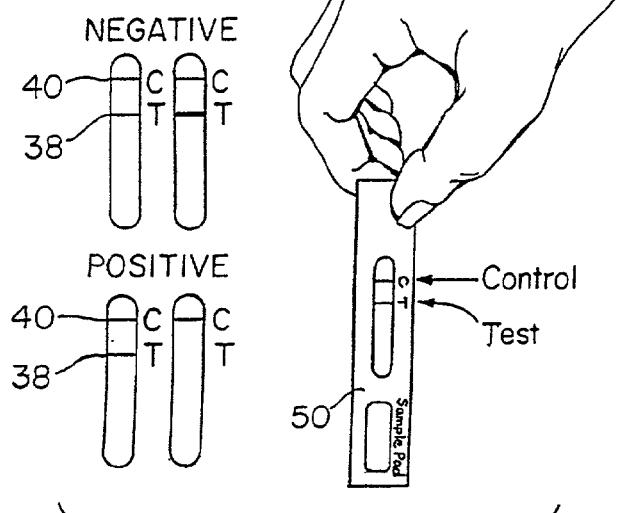
FIG. 13 is an enlarged, front-plan view of the test strip of FIGS. 7–12, with enlarged, front, sectional views of positive and negative test results.
Figure 12:
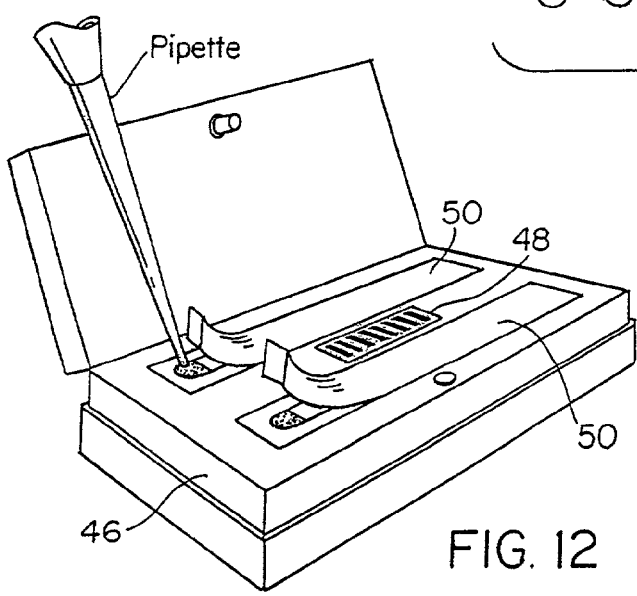

FIG. 11 illustrates test device 50 upside down and placed in one of two cavities 47 in incubator 46. FIG. 12 illustrates the technique of adding the liquid sample with a pipet, while peel tab 54 is pulled away from the end of test device 50 in incubator 46. Test device 50 is sealed and incubated. The test results of the completed test can then be read through a transparent top cover of blister package 56, as shown in FIG. 13, to provide positive or negative test results.

Inhibition assay test strip 28 (FIG. 7) selected for beta-lactams in milk is a quick test for beta-lactams in commingled raw and pasteurized milk. In operation, temperature gauge 48 in incubator 46 is checked to ensure an incubator temperature of about 55° C. For example, temperature indicator 48 may be colored, for example, green, for use. Test device 50 is placed in one cavity 47 of incubator 46 with the flat side facing up and peel tab 54 peeled back enough to expose sponge 32, for example, one centimeter. The milk is mixed thoroughly before testing, and about 0.2–0.7 ml, preferably 0.3–0.5 ml, is added by pipet to exposed sponge 32. Adhesive tape tab 54 is resealed by hand pressure and incubator 46 cover is closed. Test device 50 is incubated, for example, at least 6 to 8 minutes, and then removed from incubator 46 and held vertically and a comparison made within about one hour between test zone 38 and control zone 40. If no control zone 40 appears, the test is invalid. A negative test occurs when reference zone 38 is the same or darker than control zone 40. A positive test is indicated when test zone 38 is absent or clearly lighter than control zone 40.

In more detail, test device 10 capable of detecting analytes in biological fluids includes the following components:

Sponge 32, a compressed material, such as cellulose, is capable of absorbing a biological fluid and acting as a prefilter to remove coarse contaminants, such as hair, dirt, etc. Sponge 32 is sized to absorb a fixed amount of sample required to complete the assay. This compressed material, when expanded and contacting the inside wall of housing 12, causes sufficient pressure to drive capillary flow along the components sponge 32, mobile-phase support 33, stationary-phase membrane 36, and disposal zone 43 and in the time required (about 3 to 8 minutes) for a commercially marketable test. Sponge 32 overlaps mobile-phase support (conjugate pad) 33 by 1 to 10 mm such that, when an aqueous sample, such as milk, is added to sponge 32, the sample flows onto mobile-phase support 33.

The test device can use a biological receptor that is tagged with ample amounts of color, infrared, fluorescent or luminescent dyes. The liquified sample (e.g., milk, corn, feed, peanut extract, meat extract, serum, environmental sample, etc.) resuspends the tagged-receptor which is previously stabilized with readily soluble additives in a mobile-phase composition. The time controlled released tagged-receptor reacts with the analyte in the sample while moving into a reaction zone on stationary-phase membrane 36.

Residue specific monoclonal antibodies are also included in the mobile-phase composition to specifically bind excess residue with high sensitivity, thus, adjusting the sensitivity for those specific residues downward (to make the test less sensitive). As less of these residues are available to compete with the broad spectrum receptor, the sensitivity is adjusted closer to regulatory requirement. For example, initial sensitivity of a beta-lactam receptor to cephapirin is 3–5 ppb. Including specific antibodies to cephapirin, the sensitivity is adjusted to 15–20 ppb. Food and Drug Administration regulatory "safe" level in raw, commingled milk is 20 ppb.

Housing 12 should be used to allow for addition of biological sample, either by dipping, pouring or pipetting. Housing 12 can be constructed of a flexible or hard material, such as polystyrene, polypropylene, or polyethylene.

Mobile-phase support 33 can be made of a glass membrane or a polymer, such as polyester or polyethylene, that acts as a secondary filter for removal of less coarse materials (somatic cells). The support is pretreated with a chemical solution, such as 0.01 to 0.2 M sodium citrate pH 6–8, capable of neutralizing interferences found in biological samples. The mobile-phase support overlaps stationary-phase membrane 36 (reaction strip) by about 1 to 4 mm.

The color or fluorescent receptor/antibody-coated microspheres are suspended in a solution containing protein, e.g., albumin bovine (BSA), glycerol, sugar or equivalent thereof, e.g., sucrose (SUC) or trehalose (TRE), polyethylene glycol 8,000 MW (PEG), amino acid mixtures (AA) or detergents as stabilizers and wetting agents, and absorbed or sprayed in the membrane using a spraying instrument, such as is available from Biodot, Inc. Furthermore, the residue specific antibodies are spray dried or immobilized in this matrix. Sample buffering is also optimized here using a buffer with a given pH, salt or any required cofactor needed to optimize the receptor/antibody binding kinetic.

A mobile phase includes highly specific binding proteins, such as an enzyme, or monoclonal antibodies capable of binding to an analyte and titrated to a known concentration to make unavailable for further reaction/detection of a known amount of analyte. This unavailability for further reaction/detection allows for the adjustment of a detection level of one or more analytes to a specified level of concern. For example, in ceftiofur, a beta-lactam with a tolerance level of 50 ppb in milk, sensitivity can be changed from 5 ppb to between 40–50 ppb by the addition of a monoclonal antibody specific for ceftiofur. The specific monoclonal antibody competes with the labeled receptor to remove a specific analyte from binding to a receptor or antibody which is capable of binding to a family of related compounds.

Highly purified proteins, such as beta-lactam receptors or anti-tet IgG, prepared by affinity purification and/or a combination of hydrophobic/ion-exchange chromatography, such as a combination of hydrophobic high pressure liquid chromatography and ion exchange high pressure liquid chromatography, are attached to a colored, fluorescent, or infrared probe which can be observed by optical/instrumental means or both. Attachment of proteins to a probe is called binding protein/probe complex.

Mobile-phase composition 34, such as gold beads, is made to a particle size between 10 and 60 nm, preferably 30–40 nm. To form the beads, 1 ml of a filtered 40 mg/ml gold chloride solution is added to 360 ml of boiling water into a clean one liter flask. To 35 ml of water is added 4 ml of 1% sodium citrate solution. The citrate solution is added to the gold solution while boiling. After refluxing for 20 to 30 minutes the bead solution is cooled and brought to a pH of 7.3 with potassium carbonate.

In a specific embodiment, the receptor (960 units) in 5–20 ml of 2 mM potassium phosphate is diluted in water to 75 ml and added to the gold bead solution while mixing. This solution is incubated at 37° C. for at least one hour and generally overnight. After incubation 10% BSA (bovine serum albumin) solution is added to bring the final BSA concentration to 0.2%, and the solution is incubated for an additional 30 minutes. This bead solution is centrifuged at 8,000× g for 45 min. The bead pellet is washed and centrifuged 2 times with 10 mM potassium phosphate buffer, pH 7.2, containing 0.2% BSA and 0.05 surfactant, such as TWEEN® 20 (TWEEN® is a registered trademark of Atlas Powder Company of Wilmington, Del.) or BIO-TERGE® AS-90 (BIO-TERGE® is a registered trademark of StepHan Chemical Company of Northfield, Ill.) (sodium olefin sulfonate). The beads are then resuspended in 10 mM potassium phosphate, pH 7.2, containing 0.2% BSA, 50 mM sodium chloride, 0.05% of surfactant and preservative. Glycerol is added to the beads to give a 16.7% concentration.

Specific beta-lactam antibodies, for example, are added to the beads to target detection levels for individual beta-lactam drugs at the established safe level. Cephapirin antibody is diluted with spray solution and added to the beads to give a final concentration of about 8%. Ampicillin antibody is diluted 1 part to 9 parts with spray solution and added for a final concentration of approximately 2.85%. Ceftiofur antibody is diluted with spray solution and added to beads to a final concentration of 40% of antibody and spray solution. Two spray solutions have been used. One consists of 10 grams BSA, 2 grams saccharin, 0.05% surfactant and preservative in 10 mM sodium phosphate buffer at pH 7.4. The other consists of 10 grams BSA, 40 grams sucrose, 0.05% surfactant and preservative in 10 mM phosphate buffer at pH 7.4. For spraying, the bead solution is diluted with spray solution, usually 6 parts beads to 4 parts spray solution.

The beads can be sprayed into a mobile-phase support 33, such as a pretreated POREX® (POREX® is a registered trademark of Porex Technologies Corp. of Fairburn, Ga.) pad (treated with sodium citrate and SDS). POREX® LATERAL-FLO™ Media is a rigid pore structure made from high density polyethylene from Porex Technologies. The mobile-phase composition is diluted, for example, with 10 mM sodium phosphate buffer, pH 6.9, and sucrose to give a sucrose concentration of 4%. The mobile-phase composition is sprayed on the nitrocellulose or other suitable substrate at 0.6 μl to 1.5 μl/cm. The control zone, containing antibody to the receptor, is sprayed at the same time and the nitrocellulose is dried to 55° C. for 1 hour. Zone thickness is adjusted by added BSA to mobile-phase composition. The mobile-phase composition is sprayed, using a machine manufactured by Ivek Corporation, Biodot, Inc., or Camag Scientific, Inc. The mobile-phase composition is sprayed on the upper portion of the mobile-phase support 33, such that mobile-phase composition 34 does not overlap sponge 32, but rather mobile-phase support 33 overlaps sponge 32 by placing the topmost portion of sponge 32 about 1 to 7 mm before the sprayed portion of the mobile phase. The mobile-phase support is dried for one hour at 55° C. and tested in an assay system for sensitivity of all the drugs. Antibody concentrations in the mobile-phase composition solution are then adjusted as needed.

For the mobile phase to obtain the best color or fluorescence response, highly purified proteins (beta-lactam receptors or anti-tet IgG, for example) can be prepared by (i) affinity purification and/or (ii) a combination of hydrophobic/ion exchange chromatography. For beta-lactam receptors, for instance, the target is 50–500 units per mg protein (1 unit is equivalent to binding of 1 ng penicillin G).

For color, infrared, or fluorescent probes, the receptor/antibody can be either a color, infrared or fluorescent dye immobilized in, for example, a 0.02–10 micrometer microsphere or colloidal gold. These supports either absorb protein or exhibit functional groups, such as $NH_2$, COOH or CHO for covalent protein binding. The microsphere generally is coated with a high concentration of highly specific binding proteins.

Typically, the stationary-phase membrane is formed of nitrocellulose, nylon, polyethylene or another suitable material. In the stationary phase, the analyte representative drug is attached with a high specific ratio to a carrier, e.g., a protein such as BSA, IgG or Protein A. It is generally desirable in the stationary phase to create a molecular sieve that efficiently captures the tagged-receptor/antibody. Stationary-phase membrane 36 has multiple reaction zones present and includes test zone 38 sprayed in a line using a suitable spraying instrument. The purpose of the test zone is to capture unreacted binding protein/probe complex for viewing or measurement. Test zone 38 (FIG. 6) consists of an analyte of detection; that is, ceforanide or a member of the analyte family, that is, beta-lactams, coupled to a carrier protein, that is, BSA, IgG, KLH, suspended in a 5 to 100 mM buffer solution (such as phosphate or buffer base) at a pH range of 3–10, preferably 6–8. Total protein concentration of the antibody solution ranges from 0.2 to 100 mg/ml. The analyte-carrier, dissolved in a buffer solution, e.g., 10 mM phosphate buffer, pH 6.9 containing sugar, such as trehalose or other additives, or 0.1 M sodium bicarbonate containing sugar, such as trehalose or other additives, is sprayed as a line on the stationary-phase membrane. Tentacle immobilization of analyte conjugate to a multiple binding site carrier, such as Protein A or latex microspheres, increases stability and binding capacity. Subsequent heat treatment of the membrane further stabilizes the adhesion. On the test device, a second test zone can be added to the reaction zone to test for a second analyte. For example, the first test zone can have a first binder for amoxicillin, ampicillin, ceftiofur, cephapirin and penicillin G. The second test zone can have a second binder for cloxacillin. Alternatively, the first test zone can test for beta-lactams and the second test zone can test for sulfonamides. Additional test zones can be added to test for additional analytes.

The reaction zone also includes control zone 40, shown in FIG. 13, sprayed in a line form using a suitable spraying instrument. A purpose of control zone 40 is to capture binding protein/probe complex that has not bound to test zone 38. Control zone 40 can consist of an antibody specific to the binding protein/probe suspended in 5 to 100 mM of a buffer solution (phosphate or TRIZMA®) (TRIZMA® is a registered trademark of Sigma Chemical Company of St.

Louis, Mo.) in a pH range of 3 to 10. Total protein concentration of the antibody solution ranges generally from 0.2 to 100 mg/ml.

In one embodiment, the material for ceforanide-SH is added to the Sulfo-SMCC-BSA-NEM solution and the reaction continues with stirring overnight at 4° C. The ceforanide-BSA is dialyzed to remove free ceforanide. The control zone includes an antibody to the tagged receptor or broad spectrum antibody that is immobilized as a line parallel to the test zone. Thus, mobile-phase composition receptor/antibody captures in this line regardless of presence or lack of analyte in the sample. The control zone consists of an antibody made to the beta-lactam receptor. The receptor is purified by affinity chromatography. The antibody to the receptor is diluted in 10 mM sodium phosphate buffer and sprayed at 0.6 μl/cm to 1.5 μl/cm. Zone thickness is adjusted by adding BSA to the receptor antibody solution.

A comparison of the control zone to the test zone yields the test result. Typically, if the control zone is darker than the test zone, analyte is present at detection level or greater (see FIG. 6).

Disposal zone 43, shown in FIG. 7, typically is made of pressed cellulose or other absorbent material to keep the sample flow consistent and to retain the reacted sample. The disposal zone generally overlaps the stationary-phase membrane 36 by about 1 to 5 mm.

The mobility of the sample (milk, blood serum or other fluids) is tested to optimize reaction times and uniformity. High pore size membranes (15 to 140 μm) are used to allow flow of viscous samples, like milk or serum.

The disposal zone 43 typically includes an absorbent pad that is an absorbing membrane made of a cellulose, synthetic sponge or other material. This pad keeps the sample flowing and stops flow at saturation, thus giving the assay time control and reducing background noise.

In another specific embodiment, an aqueous biological sample is added to sponge 32 of the test device. Sponge 32 serves as a sample pad which expands as it absorbs the sample. Sponge pad 32 overlaps mobile-phase support 33, and the fluid flows onto the mobile-phase support 33 where the mobile-phase materials dissolve into the biological fluid. Analytes present in the sample begin binding with the specific binding protein(s) attached to the probe. At the same time, specific bound or unbound antibodies or binding proteins bind with specific analytes to adjust their sensitivity to the test. Mobile-phase support 33 overlaps stationary-phase membrane 36, and the biological fluid, along with mobile-phase composition 34 (colored beads), continue to react as materials flow up stationary-phase membrane 36. When the binding protein/probe complex reaches test zone 38, a portion of the binding protein/probe complex binds to the test zone. In a positive sample, analyte in the sample is bound to the binding protein/probe complex, reducing the amount of binding protein/probe complex capable of binding to the test zone 38. When the material reaches control zone 40, a portion of the binding protein/probe complex binds control zone 40. Excess reagent is then absorbed into disposal pad 43.

In a negative sample, reagents are titrated so that test zone 38 has the same or preferably a greater amount of the probe binding to it than in control zone 40. Conversely, in a positive sample, control zone 40 has a greater amount of the probe binding to it than in test zone 38.

In still another embodiment, a beta-lactam test is made to assay for beta-lactams in milk at a safe level. A partially purified beta-lactam receptor from BST (*Bacillus stearothermophilus*) is bound to a colloidal gold solution to make a beta-lactam binding protein/gold bead probe. This is sprayed on the mobile-phase support 33 along with monoclonal antibodies to ceftiofur, cephapirin, ampicillin and amoxicillin to reduce the sensitivity of these four antibiotics so that the test gives a desired dose response. On test zone 38 is sprayed a ceforanide-BSA conjugate, and to control zone 40 is sprayed an antibody to the BST beta-lactam receptor. A raw-milk sample, between 0.1–1.0 ml preferably, is applied to the sample pad by pipette, and the test strip is incubated at 55° C. After about eight minutes, test strip 10 is removed from the incubator and analyzed. If test zone 38 is darker or the same color as control zone 40 line, the sample is negative, and, if test zone 38 is lighter than control zone 40, the sample is positive.

In another embodiment, the membranes, such as the stationary phase and reaction zone membranes can be blocked, for example, with mixtures of bovine serum albumin, skim milk, polyethylene glycol, sucrose, trehalose, and amino acids to eliminate nonspecific interactions.

Test results are shown in Table 1 as follows:

TABLE 1

Beta-lactam assay in milk using lateral flow test device.

| Number of Assays | Sample | Result |
| --- | --- | --- |
| 30 | zero control | all negative |
| 10 | penicillin G at 5 ppb | all positive |
| 10 | penicillin G at 4 ppb | 5 positive, 5 negative |
| 10 | penicillin G at 3 ppb | 3 positive, 7 negative |
| 10 | ampicillin at 6 ppb | all positive |
| 10 | ampicillin at 4 ppb | all positive |
| 10 | ampicillin at 3 ppb | 5 positive, 5 negative |
| 10 | amoxicillin at 6 ppb | all positive |
| 10 | amoxicillin at 4 ppb | 8 positive, 2 negative |
| 10 | amoxicillin at 3 ppb | 4 positive, 6 negative |
| 10 | ceftiofur at 30 ppb | 3 positive, 7 negative |
| 10 | ceftiofur at 40 ppb | 8 positive, 2 negative |
| 10 | ceftiofur at 50 ppb | 10 positive |
| 10 | cephapirin at 12 ppb | 2 positive, 8 negative |
| 10 | cephapirin at 15 ppb | 5 positive, 5 negative |
| 10 | cephapirin at 20 ppb | 10 positive, 0 negative |

The described test is an inhibition-type assay. Analyte in the sample binds with a beta-lactam binding protein/mobile-phase composition probe and inhibits binding to a stationary beta-lactam bound to the surface of the membrane. Addition of a specific monoclonal antibody to ceftiofur has altered its inhibition level from approximately five ppb to between 40 and 50 ppb. Addition of a specific monoclonal antibody to cephapirin has reduced its sensitivity from approximately 3–5 ppb to between 15 to 20 ppb.

The test device of the invention can be used with test strips for detecting a variety of analytes, such as toxins, like aflatoxins, pesticides, such as organophosphates and carbamates; as well as beta-lactams, such as penicillin, ampicillin, amoxicillin, cloxacillin, dicloxacillin, oxacillin, ceftiofur, and cephapirin; tetracyclines, such as chlortetracycline, oxytetracycline and tetracycline; sulfonamides, such as sulfamethazine, sulfadimethoxine, sulfamerazine, sulfathiazole, and sulfadiazine; macrolides, such as erythromycin, spiramycin and tylosin; aminoglycosides, such as gentamicin, neomycin, and DH/streptomycin; and others such as dapsone, chloramphenicol, novobiocin, spectinomycin and trimethoprim, to detect the maximum residue-analyte limits in the sample. Most of the elements for each test are the same except the chemistries of the mobile phase, test zone and control zone, which are tailored to the specific analyte detection.

As the sample flows from stationary-phase membrane 36 into disposal zone 43 (until absorbent pad saturation), the unreacted tagged-receptor is captured in the reaction zone by an immobilized group representative analyte. Chemical residue in the sample reacts with the tagged-receptor making it unreactive to the test line. Thus, the more residue in the sample, less signal is detected in the test zone.

Stationary-phase membrane 36 is constructed from highly porous matrix suitable for viscous samples, such as milk or meat extracts. In each zone, a combination of soluble polymers is embedded (e.g., proteins, polyethylene glycol (PEG), polyvinylidene chloride (PVD), etc.) to control the kinetics of mobility of the sample from the mobile-phase composition to the reaction zone and in the reaction zone itself.

Data was generated with microbial beta-lactam receptor, specific antibodies for sulfamethazine, tetracycline and aflatoxin to detect for the presence of corresponding residues in milk or other matrices, such as serum. Levels of 3–5 ppb penicillin G (PEN G) and 5–20 ppb cephapirin, 30–100 ppb oxytetracycline (OXT), 10–100 ppb sulfamethazine (SMZ) and 2–40 ppb aflatoxin B1 were detected with these experiments.

An incubator with adjustable temperature ranging up to 70° C. generally is preferred. The test device can employ a portable calorimeter, such as is used for glucose testing, or refractive fluorometer, or infrared reader. In a preferred embodiment, the test device includes a reader that is used to read a test strip that contains two lines. The control line is a reference line that insures that the test has been run correctly. The control line is also used as a reference when the reader determines if the sample is positive or negative. The test line indicates the concentration of the substance being tested. The darker the test line the higher the concentration of the substance in the sample. The reader includes two components, a controller and a meter.

The meter reads the strip when the strip is inserted into the meter and the meter is given the command to read the strip. The meter then strobes a series of light-emitting diodes (LED), preferably, seven. The light emitted from the LED's is bounced off the strip being read. The light is then reflected onto a 128×1 Opto Sensor. The sensor sends 128 data values representing the intensity of the light at each of the 128 pixels to an on board microcontroller. The pixel data is stored in the meter's memory. The dark areas of the strip have a lower value than do the light areas. This information is later used to calculate the intensity of the two lines being read.

The controller sends a command to the meter to request the data read by the meter. The controller performs calculations on the data to determine the intensity of the two lines. If the test line is darker than the control line then the test is said to have a negative result. If the test line is lighter than the control line then the test is said to have a positive result. The controller displays to the user the result as well as a raw value representing the difference in the intensity of the two lines.

Integration of the incubator with fiber optics to read the results can provide the test with full automation.

The test unit, such as in blister pack form, is placed in an incubator which is heated to about 56.5° C.±1° C. The tape is peeled back and a liquid sample, 0.3 ml, is added to the sample well and the tape is resealed. The test unit is incubated for at least five minutes.

Once the sample is added to the sample well, it is absorbed by the sample sponge which expands inside the well. The top portion of the plastic well prevents the sponge from expanding fully. The pressure of the sponge against the well on the top and the mobile-phase support on the bottom gives some added force to propel the liquid sample up the test strip at a faster rate than would otherwise occur. The sponge expands and the sample next moves onto the mobile-phase support and interacts with the mobile-phase composition. The mobile-phase composition starts to move onto the nitrocellulose. During this time, incurred residues or analytes in the sample bind to the receptor or antibody attached to the mobile-phase conjugate.

When the mobile-phase composition reaches the test zone, the free labeled receptor binds to the test zone, resulting in a dark bottom line. Receptor or antibody with bound analyte does not bind to the test line, resulting in a noncolored or light colored test zone line. This is a sequential inhibition-type assay, where the compound of concern does not bind to the test zone. The mobile-phase composition moves past the control zone and onto an absorbent pad, which serves as a reservoir to catch unbound mobile-phase composition.

FIGS. 14–17 illustrate an embodiment of the device 101 in transparent blister package 103, which includes transparent-tape plastic seal strip 111, to enclose test strip 105 therein. Blister package 103 includes an elongated cavity to hold strip 105 and expansion cavity-housing 104 to form a generally toothbrush-shaped cavity within plastic blister package 103 and strip 105. As shown, expansion cavity-housing 104 is triangularly-shaped with a slanted, transparent housing top wall. The blister package 103 includes one movement restriction zone 114 surrounding the disposal pad 106 and another movement restriction zone 115 surrounding adhesive backing 113 at the point at which backing 113 protrudes before sample-absorbing sponge 109. Movement restriction zones 114 and 115 form pinch points which secure strip 105 within blister package 103. The device, therefore, is designed so that one location at which narrowing occurs is at disposal pad 106, in which zone there is located an absorbent material which acts as an absorbent pad. Preferably, the device is designed, and placement of components located so that, approximately one cm of adhesive backing protrudes before the sample sponge pad contained within the sample application zone. The support strip 116 is, therefore, secured in place at either one or both ends, thereby allowing unimpeded sample flow through mobile-phase membrane 108 and the stationary-phase membrane 107.

Figure 15:
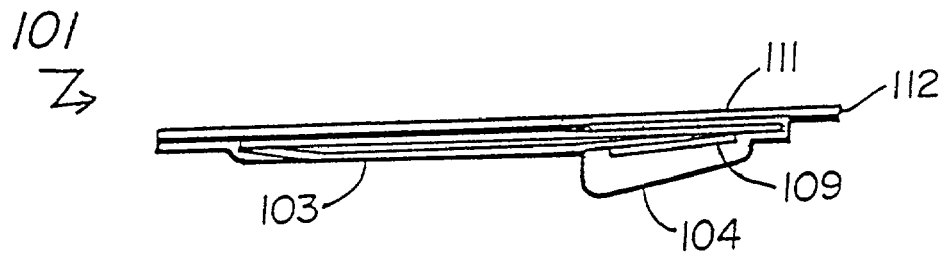
FIGS. 15, 16 and 17 are schematic, illustrative, side views of the use of the test device of FIG. 14.
Figure 16:
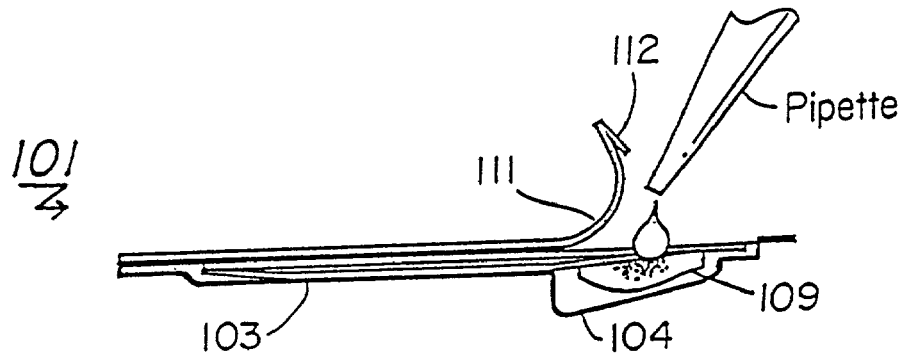
Figure 17:
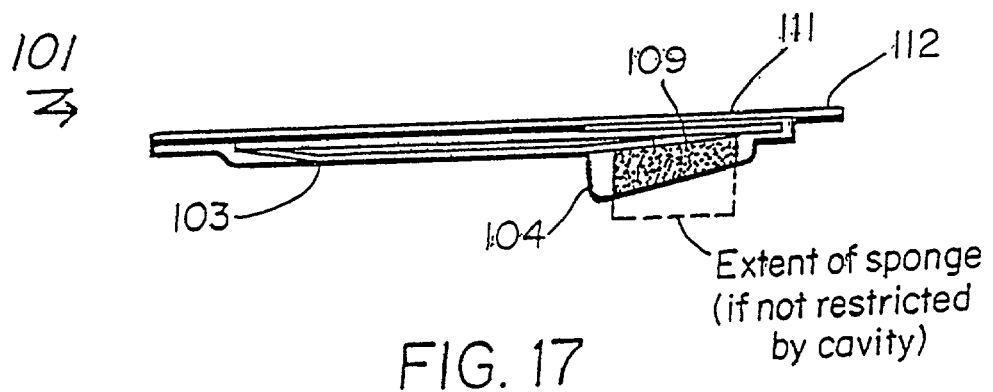

FIG. 15 shows a side sectional view of blister-package test device 101 prior to use. FIG. 15 shows blister-package test device 101 with one end peeled back by peel tab 112, to expose expansion housing cavity 104 and dry filter-absorbent sponge pad 109 of test strip 105, so that a defined amount of a liquid sample can be added, for example, by pipette, as shown. FIG. 17 illustrates test device 101 after addition of the liquid sample, and with peel tab 112 resealed and with the sponge pad 109 fully expanded by the liquid sample within housing cavity 104 and ready to incubate.

FIG. 18 is an enlarged view of absorbent pad 109 of the test device. FIG. 18 illustrates the narrowing of the inner walls of the housing in zone A, to form movement restriction zone 114, securing the adhesive backing 113, and thereby, strip 105 (not shown in FIG. 18) is held in place within the plastic blister 113. FIG. 18 also illustrates the air space zone B, existing between strip 105 and adhesive backing 113, which allows consistent flow of sample along the strip.

Figure 19:
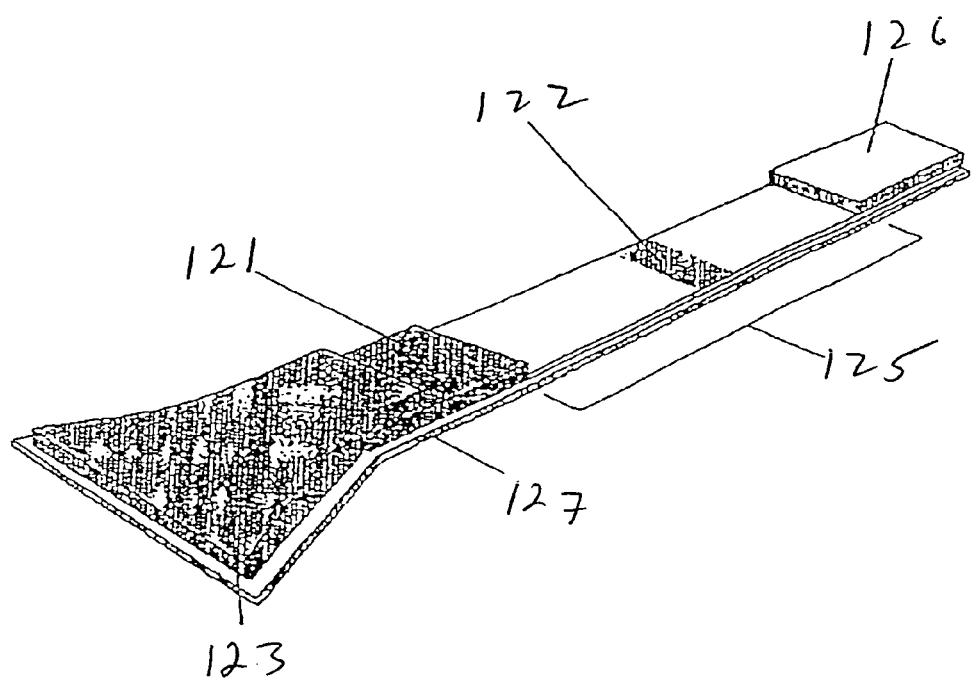
FIG. 19 illustrates an alternative test device.

FIG. 19 is an illustration of an embodiment of the test strip. The test strip can be mounted on a support 127. The sample absorbing zone 123 includes a cellulose sponge or other absorbent material capable of filtering particulates that might interfere with flow. The sample absorbing zone may also include residue specific antibodies. Sample first contacts the sample absorbing zone 123 and then flows to the releasing zone 121, for example, including biological receptors or antibody tagged with a color or fluorescent dye, and releasing zone 121. Sample flow continues to the reaction zone 125 that includes a highly porous membrane. Within the reaction zone 125 is the stationary phase 122 including an immobilized, representative, residue of target analytes. Sample flow continues to the disposal zone 126 that includes absorbent material or pad for waste management. The test device can be packaged within a device including a visualization window.

FIG. 20 illustrates an alternative packaging of the test device in the format of a standard pregnancy type test. Sample is applied to the sample absorbing zone 123 and flows to the stationary phase 122 within the reaction zone 125 where the test result is observed.

FIG. 21 illustrates an alternative embodiment of the test device within a vertical probe package allowing the test device to be dipped into the sample at the sample absorbing zone 123. The sample flows to the stationary phase 122 where the test result is observed.

FIG. 22 is a cross-section illustration of a sandwich type device including a sample absorbing zone 123, releasing zone 121, stationary phase 122, reaction zone 125 and disposal zone 126.

Figure 23:
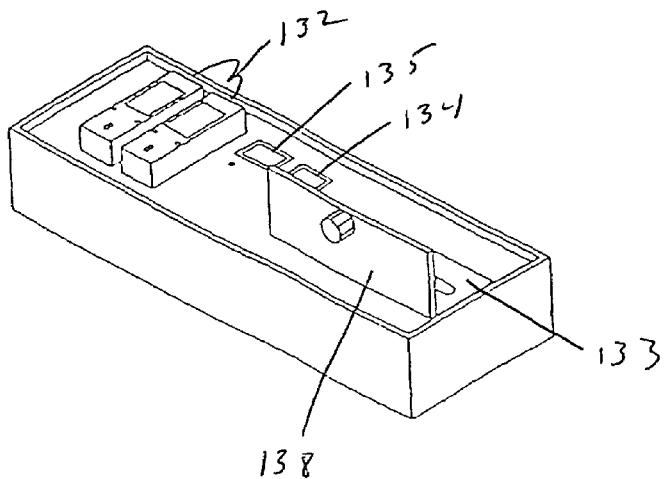
FIGS. 23, 24, and 25 are illustrative, side and top views of a combined reader and incubator embodiment.

FIG. 23 is an illustration of an embodiment of a combined sample incubator and reader. The test reader 131 is a self contained unit for detecting beta lactams or other analytes in samples. The reader includes two KEYENCE® (KEYENCE is a registered trademark of Keyence Corporation, Osaka, Japan) FS-V digital fiber optic sensors 132 and a heated sample chamber 133 to incubate the sample and read the results of the test. Separate on/off rocker switches for the incubator 134 and KEYENCE® sensors 132 are mounted on the top of the device with associated on/off indicator lights 142. The door 138 to the sample chamber 133 is located at the top of the reader 131. The sample is placed in the chamber 133 and the door 138 is shut securely. The heater is turned on and the sample is incubated. Upon completion of the incubation cycle power is applied to the sensors 132 via the reader power switch 135.

Figure 24:
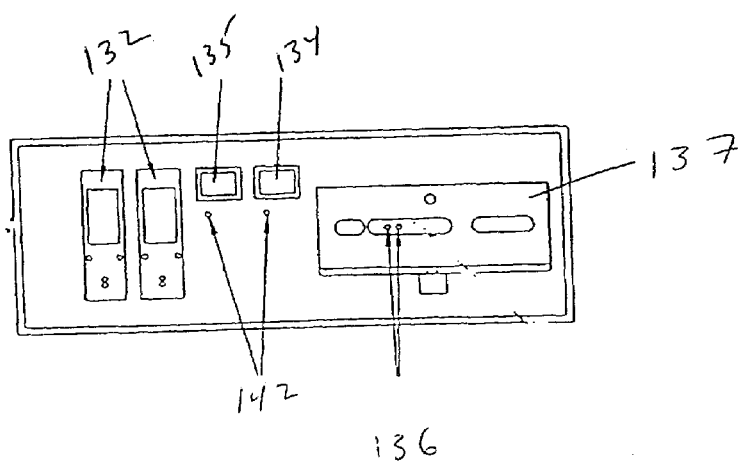

FIG. 24 is a top perspective illustration of the combined sample incubator and reader. The two fiber optic lenses 136 are mounted directly into the heater block 137 allowing the sample to be tested without being disturbed after the test has been started. The lenses 136 are attached to the KEYENCE® sensors 132 with a fiber optic cable for accurate test results.

Figure 25:
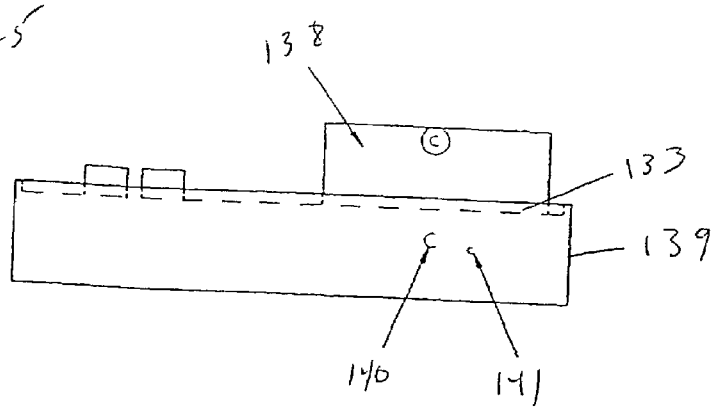

FIG. 25 is a side perspective illustration of the combined sample incubator and reader. The unit is powered by a 12 volt power supply that plugs into the end of the unit 139 and supplies 4.2 Amps. On the side of the unit is a thermostat 140 that controls the temperature of the heated sample chamber 133. The incubation temperature is set at the factory and should not require adjustment. Adjacent to thermostat 140 is a light 141 that indicates the sample chamber 133 is being brought up to operating temperature. When the light 141 is off and power is applied to the heater the sample chamber 133 is up to temperature and the test can begin. Upon test completion, the value of the control display is compared to the value of the sample display. This comparison determines if the test result is either positive or negative.

Figure 26:
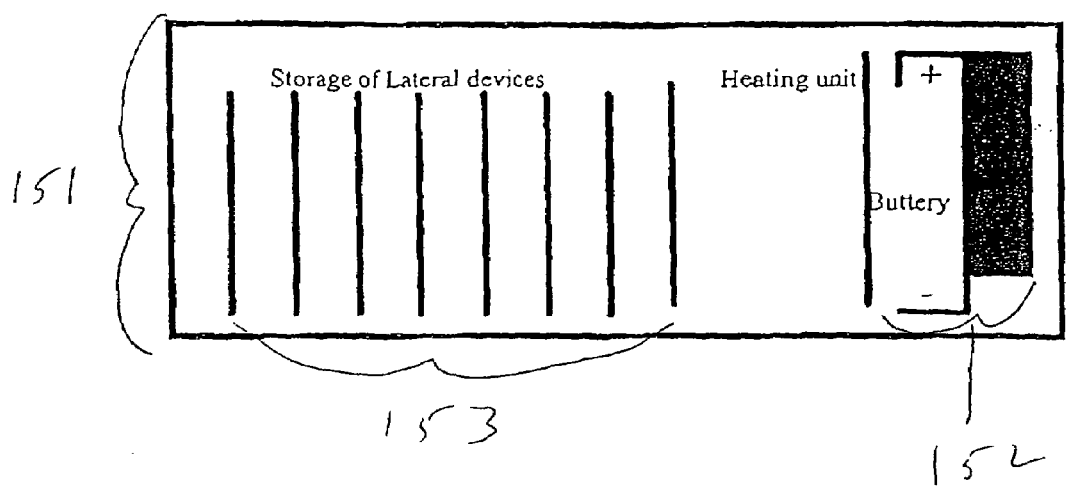
FIG. 26 is a schematic drawing of a disposable incubator and package unit for a lateral-flow diagnostic device.

FIG. 26 is a schematic drawing of a disposable incubator and package unit for one or more test strips. The unit 151 combines a small heating source 152 built in a disposable package for several lateral flow (LF) test devices 153; enough to heat a 0.01 to 1 ml sample to 20–55° C. for 4–10 minutes. The heating can be generated either by creating an electrical circuit with the lateral flow devices or by activating a chemically based heating pad. This heat source is a built-in feature of the lateral flow device package. The activation of the heating can start by insertion of the lateral flow device, into a mini-heating compartment.

The electric source should have enough power to heat 1 to 20 units. It could use a standard battery, rechargeable battery or flat battery, such as the POLAPULSE® battery from POLAROID®, (POLAPULSE AND POLAROID are registered trademarks of Polaroid Corporation, Cambridge, Mass.) or mini-heat pads such as Grabber MYCOAL® (MYCOAL is a registered trademark of Mycoal Warmers Co. Ltd, Tochigi, Japan), or as described in U.S. Pat. No. 3,976,049 or photocells for outdoor operation. In an embodiment, the disposable device includes, a heat sink/cooling mechanism, for example a piece of aluminum foil. The device can include a heat indicator, for example, a temperature sensitive reversible color device available from various sources, for example those available from Omega Engineering. This system can operate many diagnostic devices that rely on enzymatic activity to occur even under non-optimum environmental conditions such as glucose test strips, enzyme linked immunoassay, lateral diffusion assays and DNA probes.

The advantages of this built in incubator include: (i) eliminating the need for a separate portable incubator; (ii) providing more repeatable enzymatic signal than RT, even in cold weather; (iii) improved result quantification; (iv) optional temperature color indicator can eliminate the need for temperature calibration; (v) only surface contacting the heated surface is reactive; and (vi) the disposable test device and heater can be in the same package.

With optional instrumentation results can be compared to a built-in reference color. Portable hand held reader, for example glucometer type readers, can be used to obtain digital result.

The invention will now be described by the following examples:

EXAMPLE #1

Lateral-Flow Test Kit for Tetracyclines in Milk, Serum and Meat Extract

A lateral-flow test kit for tetracyclines includes: a test zone made of BSA-TET conjugate, a control line made of Goat Anti-Rabbit IgG, and a mobile phase made of Anti-TET Rabbit Antibodies-Gold conjugate BSA-TET Preparation 444.4 mg of tetracycline is dissolved in 5 ml of THF (tetrahydrofuran) and 1.5 ml of 0.2 M sodium bicarbonate is slowly added. 240.3 mg of L-Cystine are added together with 111 µl of formaldehyde 37%. The mixture is incubated at 40° C. for 30 minutes and placed on a shaker at room temperature for 2 hours. The mixture is centrifuged at 4,000 rpm for 3 minutes. A minimum yield of 60% product is verified by HPLC (high performance liquid chromatography). 463 mg of DL-Dithiothreitol is then added to the supernatant. The mixture is placed on a shaker at room temperature for 30 minutes and centrifuged at 4,000 rpm for 3 minutes. The supernatant is precipitated into acetone and the TET-CYS (tetracycline-cysteine) precipitate collected, washed and dried under nitrogen. 1.0 g of protease-free BSA is dissolved in 8 ml of 50 mM sodium phosphate pH 7.2. Twenty mg of N-Methylmaleimide is added and the mixture is placed on a shaker at room temperature for 2 hours. The mixture is dialyzed at 4° C. against 10 mM sodium phosphate pH 7.2. Fifty mg of Sulfo-SMCC is added to a volume of NEM-BSA (N-ethylmaleimide-BSA) containing 365 mg of protein. The mixture is placed on a shaker at room temperature for 2 hours. The mixture dialyzed at 4° C. against 50 mM sodium phosphate pH 7.1 (2 L×4 hours×4 changes). TET-CYS is dissolved in a volume of NEM-BSA-Sulfo-SMCC containing 150 mg of protein. Sufficient 50 mM sodium phosphate pH 7.1 buffer is added to the combined solution to get a protein concentration of 50 mg/ml. The tube is placed on a shaker at room temperature for 2 hours. BSA-TET mixture is purified with 5 mM sodium phosphate pH 6.8 using a Bio-Rad 10DG Eco-Pac Desalting Column (cut-off at 6,000 daltons). All the protein containing fractions are combined and tested for protein (using Bio-Rad Standard Protein Assay) and tetracycline activity (using a Charm II tetracycline assay). A minimum of 2 units/µg is required. BSA-TET is kept at a temperature of −20° C.

Affinity Purification of Anti-Tet IgG

CLT-COOH (chlortetracyline-COOH) Preparation 239 mg of Chlortetracycline HCL are dissolved in a mixture of 1.5 ml of DMF (dimethylformamide) and 4 ml of 0.2 M sodium bicarbonate. 130 mg of 6-Aminocaproic Acid and 105 µl of formaldehyde 37% are added. After vortex, the mixture is incubated at 40° C. for one hour and placed at room temperature on a shaker for one hour and precipitated from acetone. This precipitate is collected and dried under nitrogen.

Gel Preparation

Sepharose EAH (from Pharmacia Biotech) are washed with 10 ml of 0.5 M NaCl pH 6.0 and is suspended in a solution of 50 mg of CLT-COOH in 2 ml of 0.5 M NaCl pH 6.0. The pH is readjusted between 4.5 to 6 and 200 µl of a solution containing 100 mg of EDC in 1 ml of 0.5 M NaCl pH 6.0 is added. The pH is adjusted to 4.5–6 and the mixture is placed on a shaker at room temperature for 20 minutes. The EDC addition is repeated two more times. The gel is poured into a suitable column and the output is collected in a test tube. The column is washed alternately using 4 ml aliquots of Binding Buffer (0.1 M TRIZMA® 0.5 M NaCl pH 8.5) and Washing Buffer (0.1 M sodium acetate 0.5 M NaCl pH 4.0). The last wash is performed using Binding Buffer and is continued until the output pH is 8.5.

Antibodies Purification

The column is loaded with a mixture of 30 ml of rabbit anti-TET serum in 30 ml of Binding Buffer. After loading, the column is washed with Binding Buffer until no protein leaks. Anti-TET specific antibodies are eluted using 1 ml aliquots of Elution Buffer (from Pierce) and collected in test tubes containing 200 µl of 1.0 M sodium phosphate pH 9.4. The elution is continued until no protein leaks. The high protein containing tubes are tested for protein using Bio-Rad Standard Protein Assay. 12 µl (microliters) of a 10% BSA solution are added to each tube.

The fractions are dialyzed against 20 mM sodium phosphate and tested for specific activity using either a lateral-flow test or a Charm II tetracycline assay. An activity greater than 100 units/mg is required.

Gold Preparation 200 ml of HPLC water are boiled in a 500 ml Erlenmeyer wrapped in aluminum foil. 4 ml of 1% Gold Chloride are added to the boiling water and the solution is mixed for 3 minutes. 12 ml of 1% trisodium citrate are added to the boiling solution. Vigorous mixing is continued for an additional 3 minutes. The flask is removed from the hot plate and allowed to cool to room temperature.

Gold-Antibodies Conjugation

Ten ml of 20 mM Borate are added to 100 ml of gold. 2.5 ml of an appropriate dilution of affinity purified antibodies in 20 mM sodium phosphate 0.15 M NaCl pH 7.3 are slowly added. The solution is thoroughly mixed for 30 minutes at room temperature. 10 ml of a solution containing 10% of BSA in 2 mM Borate are added and the mixing is continued for 30 minutes. The solution is dispensed in 4×50 ml centrifuge tubes and centrifuged at 15,000 rpm for 1 hour at 10° C. The supernatant is discarded and the pellet is resuspended in a solution containing 0.1% BSA in 2 mM Borate. The solution is centrifuged again and the pellet resuspended to a final absorbance of 30 at 520 nm. 20% of glycerol and 0.05% $NaN_3$ are added and the solution is kept at −20° C.

Test Zone (BSA-TET)

BSA-TET conjugate is sprayed in the nitrocellulose at a concentration of 5 mg/ml in a 5 mM sodium phosphate pH 6.8 solution containing 10 mM dipotassium oxalate, 4% sucrose and 0.6% BSA. The volume sprayed is about 0.6 to 1.0 µl/cm.

Control Zone: Goat Anti-Rabbit IgG

The solution for the control zone consists of a mixture of 2–10% Goat Anti-Rabbit IgG (from Sigma) in a 5 mM phosphate pH 6.8 buffer containing 30 mg/ml BSA. The volume sprayed in the nitrocellulose is 1.5 µl/cm.

Mobile Phase (Anti-TET IgG—Gold Conjugate)

Anti-TET Antibodies—Gold conjugate is sprayed in the treated mobile-phase support in a solution containing 60% of gold conjugate/glycerol and 40% of diluent (10% BSA and 40% sucrose in 10 mM sodium phosphate pH 7.4). The volume sprayed is 2–5 µl/cm.

TABLE 2

Test Performance: Dose Response Curve for M.R.L.-TET (n = 6)
Level for multiresidue limit.:
Oxytetracycline (OXT) 100 ppb
Chlortetracycline (CLT) 100 ppb
Tetracycline (TET) 100 ppb

| Drug (in ppb) | % Negative | % Positive |
|---|---|---|
| Negative | 100 | 0 |
| OXT 100 | 0 | 100 |
| OXT 60 | 33 | 66 |
| OXT 30 | 50 | 50 |
| OXT 10 | 83 | 17 |
| CLT 100 | 0 | 100 |
| CLT 60 | 50 | 50 |
| CLT 30 | 66 | 33 |
| CLT 10 | 83 | 17 |
| TET 100 | 0 | 100 |
| TET 60 | 0 | 100 |
| TET 30 | 0 | 100 |
| TET 10 | 83 | 17 |
| TET 5 | 100 | 0 |

EXAMPLE 2

Lateral-Flow Test Kit for Quinolone in Milk, Meat or Serum

The lateral-flow test kit for quinolone includes: a test zone made of BSA-quinolone conjugate, a control zone made of Goat Anti-Rabbit IgG, and a mobile phase made of Anti-quinolone antibodies—Gold conjugate.

Test Zone: BSA-QUINOLONE Conjugate Formation

Quinolone BSA Preparation

Specific Conjugate (or Immunogen)

The following conjugation links the carboxylic acid of quinolones to the primary amine group on proteins. For immunogen, KLH (keyhole limpet hemocyanin) or OVA (ovalbumin) can be used while for the assay BSA is used. 40 mg ciprofloxacin or enrofloxacin are dissolved in water or DMSO (dimethylsulfoxide) respectively, and then added drop wise to a stirred BSA solution (100 mg/10 ml 0.1M MES buffer, pH 4.7). 100 mg of 1-ethyl-3[-dimethylaminopropyl] carbodiimide hydrochloride (EDC) are added and the solution is stirred for 2 hours at RT in the dark. The product is then dialyzed 3 times against 1000 ml of 20 mM phosphate buffer pH 7.2, 150 mM NaCl. Unreacted quinolone can be monitored by TLC (thin layer chromatography) using Silica Gel F and methylene chloride:methanol:acetic acid (15:5:0.1). BSA-quinolone conjugate can be visualized at the start line while unreacted quinolone moves to about Rf of 0.4.

Broad Spectrum Conjugate

In this embodiment, the quinolones are linked through the secondary amine on the piperazinyl moiety to a free sulfydryl group on the protein. Sulfosuccinimidyl 4-[N-maleimidonmethyl]-cyclohexane-1carboxylate (Sulfo-SMCC) is used for this reaction. BSA (100 mg) is first treated with 5 molar excess of Traut's reagent (2-iminothiolane*HCl) to convert primary amines to sulfydryl group at pH 7–10. After dialysis the modified BSA is combined with ciprofloxacin (50 mg) and Sulfo-SMCC (20 mg), mixed on shaker at RT for 2 hours. The BSA-N-ciprofloxacin is dialyzed at 4° C. against 50 mM sodium phosphate pH 7.1 (2 L×4 hours×4 changes). The protein concentration is adjusted to 20 mg/ml BSA with ultrafilter using Bio-Rad Standard Protein Assay. Conjugate is kept at a temperature of −20° C.

Test Zone Formation

BSA-QUINOLONE conjugate is sprayed in the nitrocellulose at a concentration of 5–20 mg/ml protein in 1–3% BSA or/and 1–4% sucrose. The volume sprayed is 1–1.5 μl/cm.

Control Zone: Goat Anti-Rabbit IgG

The solution is prepared the same as described above in the tetracylines example.

Mobile Phase: Rabbit Anti-QUINOLONE Antibodies—Gold Conjugate

Antibodies Affinity Purification

Gel Preparation

For preparation of ciprofloxacin/enrofloxacin specific antibodies, 3 ml of 4B Sepharose EAH (from Pharmacia Biotech) are suspended in 10 ml of 0.5 M NaCl pH 6.0. After vortex, the mixture is centrifuged at 3,400 rpm for 5 minutes and the supernatant discarded. The wash is repeated 4 times. 3 g of the gel is suspended in a solution, 100 mg of EDC in 1 ml of DMSO is added, and the mixture is placed on a shaker at room temperature for 20 minutes. The EDC addition is repeated two more times.

The gel is poured into a suitable column and the output is collected in a test tube. The column is washed alternately using 4 ml aliquots of Binding Buffer (0.1 M TRIZMA® 0.5 M NaCl pH 8.5) and Washing Buffer (0.1 M sodium acetate 0.5 M NaCl pH 4). Each wash is eluted into a clean test tube. The fluorescence of the output at 366 nm is monitored and the washings continued until no fluorescence is visible. The last wash is performed using Binding Buffer and is continued until the output pH is 8.5.

Antibodies Purification

The column is loaded with a mixture of 30 ml of rabbit anti-enrofloxacin serum in 30 ml of Binding Buffer. After loading, the column is washed with Binding Buffer until no protein leaks. Anti-quinolone specific antibodies are eluted using 1 ml aliquots of Elution buffer (from Pierce) and collected in test tubes containing 200 μl of 1.0 M sodium phosphate tubes and are tested for protein using Bio-Rad Standard Protein Assay. 12 μl of a 10% BSA solution are added to each tube.

The fractions are tested for specific activity using a lateral-flow test strip assay with 40 nm gold beads. The antibodies are dialyzed against 20 mM phosphate buffer, 150 mM NaCl and kept at −20° C.

For preparation of broad spectrum antibodies, 100 mg of sarafloxacin are dissolved in a 5 ml DMSO and pass through Pharmacia HiTrap NHS activated cartridge. After 1 hour excess sarafloxacin is washed with DMSO followed by 50 mM phosphate buffer pH 7.2.

The column is washed alternately using 4 ml aliquots of Binding Buffer (0.1 M TRIZMA® 0.5 M NaCl pH 8.5) and Washing Buffer (0.1 M sodium acetate 0.5 M NaCl pH 4.0). Each wash is eluted into a clean test tube. The color of the output is monitored and the washings continued until no color leaks. The last wash is performed using Binding Buffer and is continued until the output pH is 8.5.

Antibodies Purification

The column is loaded with a mixture of 30 ml of rabbit anti-enrofloxacin serum in 30 ml of Binding Buffer. After loading, the column is washed with Binding Buffer until no protein leaks. Anti-quinolone specific antibodies are eluted using 1 ml aliquots of Elution Buffer (from Pierce) and collected in test tubes containing 200 μl of 1.0 M sodium phosphate pH 9.4. The elution is continued until no protein leaks. The high protein-containing tubes are tested for protein using Bio-Rad Standard Protein Assay. 12 μl of a 10% BSA solution are added to each tube.

The fractions are tested for specific activity using either a lateral-flow test or a tetracycline assay. An activity of greater than 100 units/mg is preferred. The antibodies are kept at a temperature of −20° C. The column is regenerated by washing alternately with 4 ml of Pierce Elution Buffer and 4 ml of Binding Buffer (3 cycles).

Gold Bead Preparation

Gold bead preparation is conducted by the same method as described above in the tetracyclines example.

Gold-Antibodies Conjugation

Gold-Antibodies conjugation is conducted by the same method as described above in the tetracyclines example.

Spraying

Antibodies-Gold conjugate is sprayed in the treated mobile-phase support in a solution containing gold conjugate in final 5% BSA and 20% sucrose. The volume sprayed is 2–10 microliters per cm.

TABLE 3

Test Performance: Dose Response Curve for Quinolones
Target levels for multiresidue limit are in milk:
Ciprofloxacin and enrofloxacin 10 ppb
in meat: Ciprofloxacin and enrofloxacin 30 ppb

| Toxin levels (in ppb) | Estimated % Negative | Estimated % Positive |
|---|---|---|
| Negative - Milk | 100 | 0 |
| Enrofloxacin 30 | 0 | 100 |
| Enrofloxacin 10 | 0 | 100 |
| Enrofloxacin 5.0 | 10 | 90 |
| Enrofloxacin 2.5 | 75 | 25 |
| Enrofloxacine 1.0 | 100 | 0 |
| Ciprofloxacin 30 | 0 | 100 |
| Ciprofloxacin 10 | 0 | 100 |
| Ciprofloxacin 5.0 | 10 | 90 |
| Ciprofloxacin 2.5 | 75 | 25 |
| Ciprofloxacin 1.0 | 100 | 0 |
| Negative - Meat | 100 | 0 |
| Enrofloxacin 30 | 0 | 100 |
| Enrofloxacin 15 | 10 | 90 |

EXAMPLE 3

Lateral-Flow Test for Aflatoxin in Milk, Feed, Corn, and Peanut Extract

Construction of the aflatoxin test device is common with the beta-lactam lateral-flow device. Some modifications are required for adapting the assay to various matrices, e.g., milk, feed extracts, etc.

The lateral-flow test for aflatoxin includes: a test zone made of BSA-aflatoxin conjugate, a control zone made of Goat Anti-Rabbit IgG, and a mobile phase made of anti-aflatoxin antibodies—Gold conjugate.

Mobile Phase Construction

Broad spectrum Rabbit anti-aflatoxin antibodies are prepared using Protein A affinity chromatography. The preferred antibodies are those with good cross-reactivity to aflatoxin B1, M1, G1, B2, G2.

Colloidal gold 10 to 50 nm is prepared at 2 $OD_{540}$ and coated with a precalibrated amount of purified antibodies as described for the tetracycline test. The colloidal gold beads are further stabilized with 1% bovine serum albumin, washed twice in 2 mM Borax/1% BSA and concentrated to about 30 $OD_{540}$ with glycerol (final concentration of 30%). They can be kept at –20° C. for at least one year.

For spraying, the antibody-coated gold beads are suspended in a solution containing protein, e.g., albumin bovine (BSA) at 10%, sucrose at 40% or polyethylene glycol 3550 MW at 10 to 40% and sprayed in pretreated mobile-support phase as a 5 mm band at about 1 µl/cm. The mobile-support phase is then dried at 37 to 55° C. for up to 2 hours.

Pre-Treated Mobile Support

Mobile-support phase strips are soaked (50 strips per liter) for 2 hours in a solution of: 0.5% BSA, 0.5% sucrose, 0.5% TWEEN® 20, 0.01% SDS, and 2 mM Borax.

Excess solution is removed by dripping and strips are hung horizontally at 55° C. for drying for at least 4 hours and preferably overnight.

Stationary Phase—Test Zone

Aflatoxin B1 is chemically attached to BSA, or OVA or another protein. The objective is a ratio of 2 to 10 moles of aflatoxin B1 to mole BSA. The BSA-aflatoxin B1 conjugate is then mixed with carrier protein (0.1 to 2%) and sugar or PEG (1 to 5%) or glycerol (10 to 30%) and kept at –20° C. The conjugate solution is applied to the nitrocellulose strip at 0.5 to 2 µl/cm (or 2–20 ng total Aflatoxin B1 per cm). Heat treatment of the membrane at 55° C. stabilizes the test zone construction. This creates a stationary phase with a molecular sieve that efficiently interacts and captures aflatoxin-free, anti-aflatoxin-tagged gold beads. During the test, the sugar and/or PEG and/or glycerol in the test zone are dissolved by the advancing sample fluid leaving a porous 3D-type structure with highly effective analyte sites to bind the antibody-tagged gold beads.

Control Zone—Reference Zone

A pure Goat Anti-Rabbit IgG is immobilized as a line parallel to the test zone. The Goat Anti-Rabbit IgG is applied to the nitrocellulose in similar solutions as the test zone at a precalibrated concentration of 1 to 10% to create a binding sieve of the anti-aflatoxin-tagged gold beads equivalent to the test zone. This zone captures anti-aflatoxin-tagged gold beads regardless of presence or lack of bound aflatoxin.

Matrices:

Milk: homogenized and raw milk can be tested directly in the device at 35 to 55° C. Grain, nuts, Feed Testing: For example 50 gm corn is homogenized in 100 ml 80% methanol. The extract is filtered, centrifuged or let stand for 10 minutes to clarify. The extract is then diluted 1 to 7 in a buffer, containing 25 mM phosphates pH 7.4 and 2% bovine serum albumin or milk powder. Sample of 0.3 ml of diluted extract is added to the lateral-flow device. Assay develops at 45° C. within 3 to 8 minutes.

TABLE 4

Test Performance for Aflatoxin

| Toxin levels (in ppb) | Estimated % Negative | Estimated % Positive |
|---|---|---|
| Negative - FEED | 100 | 0 |
| Aflatoxin B1 30 | 0 | 100 |
| Aflatoxin B1 20 | 0 | 100 |
| Aflatoxin B1 10 | 0 | 100 |
| Aflatoxin B1 5 | 70 | 30 |
| Aflatoxin B1 1 | 0 | 100 |
| Negative - MILK | 100 | 0 |
| Aflatoxin M1 0.5 | 100 | 0 |
| Aflatoxin M1 0.25 | 100 | 0 |
| Aflatoxin M1 0.1 | 60 | 40 |

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method for determining whether one or more members of an analyte family is present in a test sample at or above a predetermined threshold level, wherein the predetermined threshold level for one member of said analyte family differs from the predetermined threshold level for at least one other member of said analyte family, said method comprising the steps of:
   (a) allowing said sample to contact a receptor, wherein said receptor is characterized by an ability to bind to at least two members of said analyte family, so as to allow said receptor to bind said at least two members of said analyte family in said sample, if present, to form an analyte-receptor complex with said present member, whereby said method has an initial analyte-specific test sensitivity level for each of said at least two members respectively;
   (b) prior to, concurrently with, or subsequent to step (a), allowing said sample to contact an amount of one or more analyte-specific adjustment binders, each adjustment binder having binding specificity for at least one selected member of said analyte family but not all of said at least two members of the analyte family, said analyte-specific adjustment binder competing with said receptor for binding to said at least one selected member, the amount of each of said one or more analyte-specific adjustment binders chosen to make an amount of said at least one selected member unavailable for binding to said receptor, said amount of unavailable selected member being sufficient to adjust said selected member's respective sensitivity level to said selected member's predetermined threshold level;
   (c) subsequent to steps (a) and (b), allowing said sample to come into contact with a receptor binder on a solid support, said receptor binder characterized in that said receptor binder binds to the receptor but does not bind to the analyte-receptor complex;
   (d) prior to, concurrently with, or subsequent to steps (a)–(c), allowing said receptor to be tagged with a detectable label; and
   (e) detecting receptor bound to said receptor binder on said solid support as an inverse indication of the presence of one or more of said members of said analyte family in said sample at or above said predetermined threshold level.

2. The method of claim 1, further comprising the steps of:
   (f) subsequent to steps (a) and (b), allowing said sample to come into contact with a control binder, said control binder characterized in that it binds both to said receptor and to said analyte-receptor complex;
   (g) detecting receptor and analyte-receptor complex bound to said control binder; and
   (h) comparing binding to said control binder with binding to said receptor binder, whereby said one or more members of said analyte family is present in said sample at or above said threshold level when said binding to said control binder exceeds binding to said receptor binder.

3. The method of claim 1, wherein said receptor is an enzyme.

4. The method of claim 1, wherein said receptor is an antibody.

5. The method of claim 1, wherein said receptor is isolated from *B. stearothermophilus*.

6. The method of claim 1, further comprising a second receptor, said second receptor having binding affinity for at least one additional analyte in said sample.

7. The method of claim 1, further comprising one or more additional receptors which bind analytes within the same analyte family to which the first receptor is able to bind, said additional receptor having a different sensitivity for one or more analytes within said analyte family as compared to said first receptor.

8. The method of claim 7, wherein said additional receptor binds to cloxacillin.

9. The method of claim 1, wherein the receptor binder comprises an analyte conjugate.

10. The method of claim 1, wherein said receptor binder comprises ceforanide linked to a protein.

11. The method of claim 2, wherein said control binder is a rabbit anti-receptor antibody.

12. The method of claim 1, wherein said sample is allowed to contact said receptor at a temperature of 30° C. or greater.

13. The method of claim 1, wherein said adjustment binder is selected from the group consisting of an enzyme, a receptor, and an antibody.

14. The method of claim 1, wherein the adjustment binder is specific for an analyte selected from the group consisting of ceftiofur, cephapirin, amoxicillin, ampicillin and penicillin.

15. The method of claim 1, wherein the adjustment binder is specific for cloxacillin.

16. The method of claim 1, wherein the sample is allowed to contact the adjustment binder prior to contact with the receptor.

17. The method of claim 1, wherein a result that said analyte is present in said sample at or above a threshold level is a positive result, and a positive does not differentiate one particular analyte from another.

18. The method of claim 1, wherein the receptor is bound to detectable microparticles.

19. The method of claim 1, wherein the receptor comprises protein-coated, gold microsphere beads.

20. The method of claim 1, wherein the method detects cephapirin at a sensitivity of about 15 to 20 ppb.

21. The method of claim 1, wherein the method detects ceftiofur at a sensitivity of about 40 to 50 ppb.

22. The method of claim 1, wherein said analyte is a toxin.

23. The method of claim 1, wherein said analyte is a beta lactam.

24. The method of claim 1, wherein said analyte is a tetracycline.

25. The method of claim 1, wherein said analyte is a sulfonamide.

26. The method of claim 1, wherein said analyte is a macrolide.

27. The method of claim 1, wherein said analyte is an aminoglycoside.

28. The method of claim 1, wherein said analyte is a quinolone.

29. The method of claim 1, wherein said analyte is a pesticide.

30. The method of claim 1, wherein said analyte is a microorganism.

31. The method of claim 1, wherein said method further comprises the steps of:
   (a) providing a test device, said test device comprising:
      (i) a support strip;
      (ii) a sample-absorbing matrix attached to said support strip, said sample-absorbing matrix having material for absorbing an amount of the sample;
      (iii) a mobile-phase support for holding a mobile-phase composition, said mobile-phase support and mobile-phase composition being in fluid communication with said sample absorbing matrix, wherein said mobile-phase composition comprises said receptor and one or more of said analyte-specific adjustment binders;
(iv) a stationary-phase membrane in contact with the mobile-phase support and having a first end and a second end, wherein said membrane allows lateral capillary flow of the sample from the first end to the second end; and
(v) at least one test zone on the membrane having said receptor binder bound to said membrane; and
(b) applying said sample to said sample-absorbing matrix.

32. The method of claim 31, wherein said test device further comprises a control zone on the membrane, said control zone comprising a control binder characterized in that it binds both to said receptor and to said analyte-receptor complex, said method further comprising the step of detecting receptor and analyte-receptor complex bound to said control binder at said control zone.

33. The method of claim 31, wherein the sample-absorbing matrix includes a dry, compressed, cellulosic-membrane material.

34. The method of claim 31, wherein said test device further includes a disposal zone at the second end.

35. The method of claim 31, wherein said test device further includes an elongate blister housing enclosing said support strip, sample-absorbing matrix, mobile-phase support, mobile-phase composition, stationary-phase membrane, test zone and control zone, said elongate blister housing defining an elongated strip cavity having a first end and a second end.

36. The method of claim 35, wherein the elongated blister housing comprises a transparent blister housing secured to a tape strip having a peelable end tab.

37. The method of claim 35, wherein said elongate blister housing includes a transparent, top-cover section to allow observation of test results on the test device.

38. The method of claim 35, wherein said elongate blister housing is characterized by an expansion cavity housing at the one end and extending outwardly from a top cover.

39. The method of claim 38, wherein the expansion cavity includes a top cover which has one or more apertures therein to increase the penetration efficiency of the liquid sample into the sample-absorbing matrix.

40. The method of claim 35, wherein the elongate blister housing is formed of a transparent plastic material.

41. The method of claim 35, wherein the first end comprises a means for sealing an expansion cavity.

42. The method of claim 35, wherein the elongated blister housing includes an expansion cavity at the one end of the housing and opposite to the sample-absorbing matrix, to permit selected expansion of the sample-absorbing matrix to fill the expansion cavity.

43. The method of claim 32, wherein said detecting comprises observing a signal, said method further comprising the step of comparing the detectable signal of the control zone to the detectable signal of the test zone, the test device arranged and constructed to provide a positive or negative result when a member of the analyte family is present at or above a threshold level, said member having a threshold level which is different from the threshold level of other members of the analyte family, said positive result indicated by a more intense signal in the control zone as compared to the test zone and said negative result indicated by a less intense signal in the control zone as compared to the test zone.

44. The method of claim 2, further comprising the step of using a reader for said comparing.

45. The method of claim 31, wherein said mobile-phase composition further comprises one or more additional receptors which bind analytes within the same analyte family to which the first receptor is able to bind, said additional receptor having a different sensitivity for one or more analytes within said analyte family as compared to said first receptor.

46. The method of claim 31, wherein said mobile-phase composition further comprises a second receptor, said second receptor having binding affinity for at least one additional analyte in said sample.

47. The method of claim 46, wherein said device comprises at least two test zones, wherein a first test zone of said test zones comprises a first receptor binder characterized in that said first receptor binder binds to said first receptor but does not bind to the analyte receptor-complex, and wherein a second test zone of said test zones comprises a second receptor binder characterized in that said second receptor binder binds to the second receptor but does not bind to the analyte-receptor complex.

* * * * *